United States Patent
Wang et al.

(10) Patent No.: US 7,791,013 B2
(45) Date of Patent: Sep. 7, 2010

(54) BIOLOGICAL MICROARRAY LINE SCANNING METHOD AND SYSTEM

(75) Inventors: Mark Wang, San Diego, CA (US);
Wenyi Feng, San Diego, CA (US);
Robert Kain, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 762 days.

(21) Appl. No.: 11/602,887

(22) Filed: Nov. 21, 2006

(65) Prior Publication Data

US 2008/0117518 A1    May 22, 2008

(51) Int. Cl.
G02B 27/10    (2006.01)
(52) U.S. Cl. .............................. 250/222.1; 250/227.11; 250/576
(58) Field of Classification Search ............... 250/222.1, 250/227.11
See application file for complete search history.

(56) References Cited

U.S. PATENT DOCUMENTS

| | | | |
|---|---|---|---|
| 4,204,230 A | 5/1980 | Sprague |
| 4,382,267 A | 5/1983 | Angle |
| 4,700,298 A | 10/1987 | Palcic et al. |
| 4,826,299 A | 5/1989 | Powell |
| 4,845,552 A | 7/1989 | Jaggi et al. |
| 4,877,326 A | 10/1989 | Chadwick et al. |
| 5,159,199 A | 10/1992 | LaBaw |
| 5,173,748 A | 12/1992 | Bilhorn |
| 5,528,050 A | 6/1996 | Miller et al. |
| 5,578,818 A | 11/1996 | Kain et al. |
| 5,585,639 A | 12/1996 | Dorsel et al. |
| 5,629,808 A | 5/1997 | Powell |
| 5,719,391 A | 2/1998 | Kain |
| 5,754,291 A | 5/1998 | Kain |
| 5,782,770 A | 7/1998 | Mooradian et al. |
| 5,837,475 A | 11/1998 | Dorsel et al. |
| 5,847,400 A | 12/1998 | Kain et al. |
| 5,945,679 A | 8/1999 | Dorsel et al. |
| 5,981,956 A | 11/1999 | Stern |
| 5,998,796 A | 12/1999 | Liu et al. |
| 6,025,601 A | 2/2000 | Trulson et al. |
| 6,043,506 A | 3/2000 | Heffelfinger et al. |
| 6,043,880 A | 3/2000 | Andrews et al. |
| 6,118,127 A | 9/2000 | Liu et al. |
| 6,134,002 A | 10/2000 | Stimson et al. |
| 6,160,618 A | 12/2000 | Garner |
| 6,177,990 B1 | 1/2001 | Kain et al. |

(Continued)

OTHER PUBLICATIONS

Global Laser Product Highlights, Global Laser Technology Solutions homepage, http://www.global-lasertech.co.uk/g_mainlink.asp, May 4, 2006.

(Continued)

*Primary Examiner*—Seung C Sohn
(74) *Attorney, Agent, or Firm*—Fletcher Yoder PC

(57) ABSTRACT

A line scanning arrangement for imaging microarrays includes a line illuminator that converts output from one or more lasers to a radiation line. The laser output passes through a single mode fiber and a module that converts the laser light to the radiation line. The line is confocally directed to sites on the microarray, and retrobeams returned from the sites are collected on an imaging detector. The microarray is moved in the imaging apparatus so as to progressively illuminate an array or matrix of sites for imaging.

44 Claims, 19 Drawing Sheets

U.S. PATENT DOCUMENTS

| | | | |
|---|---|---|---|
| 6,207,960 | B1 | 3/2001 | Stern |
| 6,225,625 | B1 | 5/2001 | Pirrung et al. |
| 6,229,635 | B1 | 5/2001 | Wulf et al. |
| 6,245,507 | B1 | 6/2001 | Bogdanov |
| 6,252,236 | B1 | 6/2001 | Trulson et al. |
| 6,309,601 | B1 | 10/2001 | Juncosa et al. |
| 6,371,370 | B2 | 4/2002 | Sadler et al. |
| 6,388,788 | B1 | 5/2002 | Harris et al. |
| 6,400,487 | B1 | 6/2002 | Harris et al. |
| 6,403,957 | B1 | 6/2002 | Fodor et al. |
| 6,441,379 | B1 | 8/2002 | Osgood et al. |
| 6,495,363 | B2 | 12/2002 | Bogdanov |
| 6,545,264 | B1 | 4/2003 | Stern |
| 6,590,689 | B1 | 7/2003 | Dorsel |
| 6,592,036 | B2 | 7/2003 | Sadler et al. |
| 6,597,000 | B2 | 7/2003 | Stern |
| 6,650,411 | B2 | 11/2003 | Odoy et al. |
| 6,678,048 | B1 | 1/2004 | Rienstra et al. |
| 6,687,000 | B1 | 2/2004 | White |
| 6,741,344 | B1 | 5/2004 | Stern et al. |
| 6,813,018 | B2 | 11/2004 | Richman |
| 6,825,930 | B2 | 11/2004 | Cronin et al. |
| 6,838,650 | B1 | 1/2005 | Toh |
| 6,902,112 | B2 | 6/2005 | Sadler et al. |
| 7,279,323 | B2 * | 10/2007 | Ogura ................ 435/287.1 |
| 2002/0030811 | A1 | 3/2002 | Schindler |

OTHER PUBLICATIONS

SPECIM Spectral Camera User Manual, Version 1.1, Sep. 2001.

Powell, "Design of a Laser Beam Line Expander", Applied Optics, vol. 26, No. 17, Sep. 1, 1987, pp. 3705-3709.

Evangelista et al., "Confocal-Line Optical Microscopy", Optics in Complex Systems, SPIE vol. 1319, 1990, pp. 464-465.

Benedetti et al., "Confocal-Line Microscopy", Journal of Microscopy, vol. 165, Pt 1, Jan. 1992, pp. 119-129.

Benedetti et al., "Achieving Confocal-Point Performance in Confocal-Line Microscopy", Bioimaging, vol. 2, 1994, pp. 122-130.

Bewsher et al., "Design of Single-Element Laser-Beam Shape Projectors", Applied Optics, vol. 35, No. 10, Apr. 1, 1996, pp. 1654-1658.

Christensen et al., "Hyperspectral Raman Microscopic Imaging Using Powell Lens Line Illumination", Applied Spectroscopy, vol. 25, No. 9, 1998, pp. 1145-1147.

Schultz et al., "Hyperspectral Imaging: A Novel Approach for Microsopic Analysis", Cytometry, vol. 43, 2001, pp. 239-247.

Boas, "Scanning System Offers High-throughput Bioanalysis", Biophotonics International, vol. 50, 2004, pp. 50-54.

Sinclair et al., "Design, Construction, Characterization, and Application of a Hyperspectral Microarray Scanner", Applied Optics, vol. 43, No. 10, Apr. 1, 2004, pp. 2079-2088.

Hesse et al., "Single-Molecule Reader for High-Throughput Bioanalysis", Analytical Chemistry, vol. 76, 2004, pp. 5960-5964.

Im et al., "Simple High-Speed Confocal Line-Scanning Microscope", Optics Express, vol. 13, No. 13, Jun. 27, 2005, pp. 5151-5156.

Sonnleitner et al., "High-Throughput Scanning with Single-Molecule Sensitivity", SPIE vol. 5699, 2005, pp. 202-210.

Jacak et al., "Ultra-Sensitive DNA Detection on Microarrays", SPIE vol. 5699, 2005, pp. 442-449.

* cited by examiner

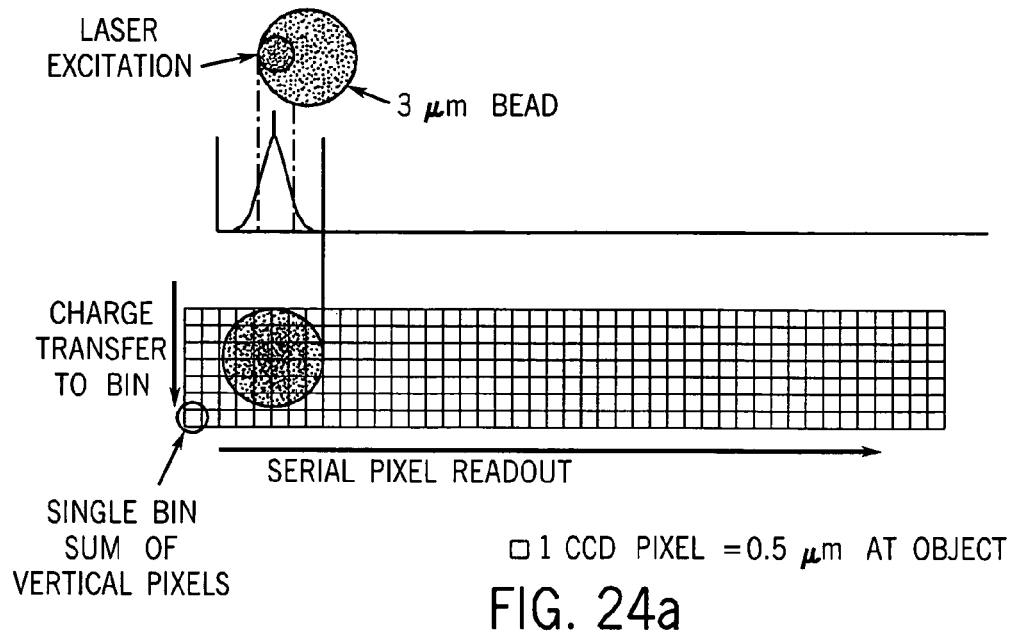
FIG. 24a
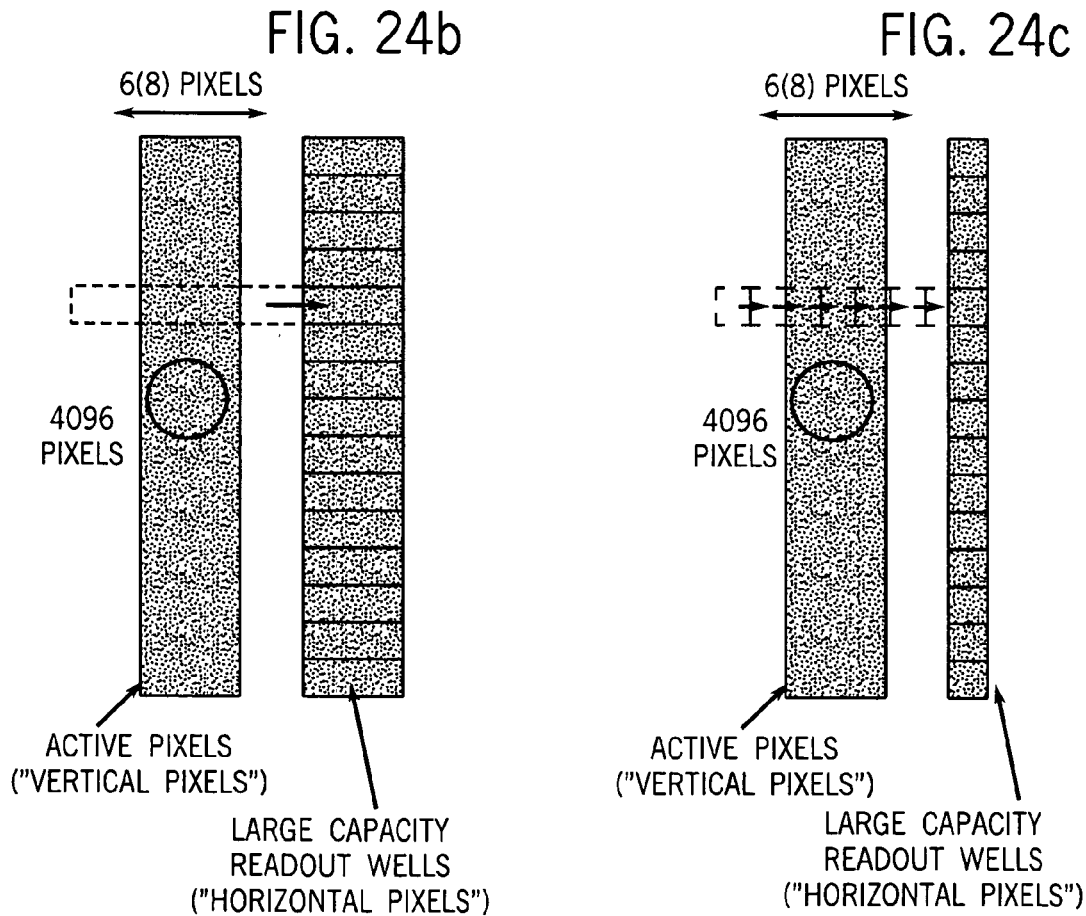
FIG. 24b
FIG. 24c

BIOLOGICAL MICROARRAY LINE SCANNING METHOD AND SYSTEM

BACKGROUND

The present invention relates generally to the field of scanners for imaging and evaluating biological microarrays. More particularly, the invention relates to a technique for rapidly and accurately evaluating microarrays through the use of confocal line scanning.

An increasing number of applications are being developed for biological microarrays. Such microarrays typically include Deoxyribonucleic Acid (DNA) and Ribonucleic Acid (RNA) probes that are specific for nucleotide sequences present in genes in humans and other organisms. Individual DNA or RNA probes can be attached at specific locations in a small geometric grid on a microarray support. A test sample, such as from a known person or organism, can be exposed to the grid, such that complimentary genes or fragments hybridize to probes at the individual sites in the array. The array can then be examined by scanning specific frequencies of light over the sites to identify which genes or fragments in the sample were present, by fluorescence of the sites at which genes or fragments hybridized.

Such microarrays, sometimes referred to as gene or genome chips, DNA chips, gene arrays, and so forth, may be used for expression profiling, monitoring expression levels, genotyping, sequencing, and so forth. For example, diagnostic uses may include evaluation of a particular patient's genetic makeup to determine whether a disease state is present or whether pre-disposition for a particular condition exists. The reading and evaluation of microarrays is a key to their utility. For example, in certain types of microarrays, DNA probes are attached to beads at individual sites in the array. Because the fragments are attached in a random or statistically varying pattern, it is necessary to image the microarray to determine the location of each of the individual fragments, and their makeup. Moreover, once a sample has been exposed to the microarray, reading the microarray is necessary to determine the makeup of the sample.

Various types of microarray readers have been proposed and are currently in use. In many such readers, a small point of light is scanned across lines of the microarray to cause fluorescence of the individual sites, particularly those sites to which genes or fragments are hybridized. Such scanning is preferably extremely fast and accurate. Current microarray designs, provide for many thousands of individual sites in a very small area of the substrate. The number of sites and the density of such sites in the array are constantly increasing, posing challenges to known scanning and imaging techniques.

There is a constant need, therefore, for improved microarray scanning and imaging technologies. There is a particular need for a technique that will allow for very fast scanning of a large number of individual sites, and that reduces the potential for errors in imaging.

BRIEF DESCRIPTION

The present invention provides a microarray scanning and imaging system designed to respond to such needs. In accordance with certain aspects of the invention, a laser light source is coupled to a single mode fiber optic cable for transmitting laser light in single mode transmission. A line illuminator converts laser light from the source to a radiation line. The line illuminator includes a collimator arranged to receive the laser light from the source and an aspherical lens for converting collimated light from the collimator to the line of radiation. A focusing device directs the line of radiation onto a plane at the surface of a microarray.

In accordance with another aspect of the invention, a similar system may include a second fiber optic cable coupled to the first single mode fiber optic cable at one end thereof and to the line illuminator at another end thereof, at least one of the fiber optic cables being a single mode fiber optic cable.

In accordance with yet another aspect of the invention, a system for imaging a microarray includes first and second laser light sources, each source configured to output laser light in a different predetermined frequency band. First and second single mode fiber optic cables are coupled to the first and second laser light sources, respectively, for transmitting laser light in single mode transmission. First and second line illuminators are coupled to the first and second single mode fiber optic cables, respectively, for converting laser light from the respective source to a line of radiation, the line illuminators each including a collimator arranged to receive the laser light from the source and an aspherical lens for converting collimated light from the collimator to the line of radiation. A focusing device, then directs the line of radiation onto a plane at the surface of a microarray.

The invention also provides methods for making and using arrangements of the type discussed above, and more particularly described in the discussion provided below.

DRAWINGS

These and other features, aspects, and advantages of the present invention will become better understood when the following detailed description is read with reference to the accompanying drawings in which like characters represent like parts throughout the drawings, wherein.

Figure 25:
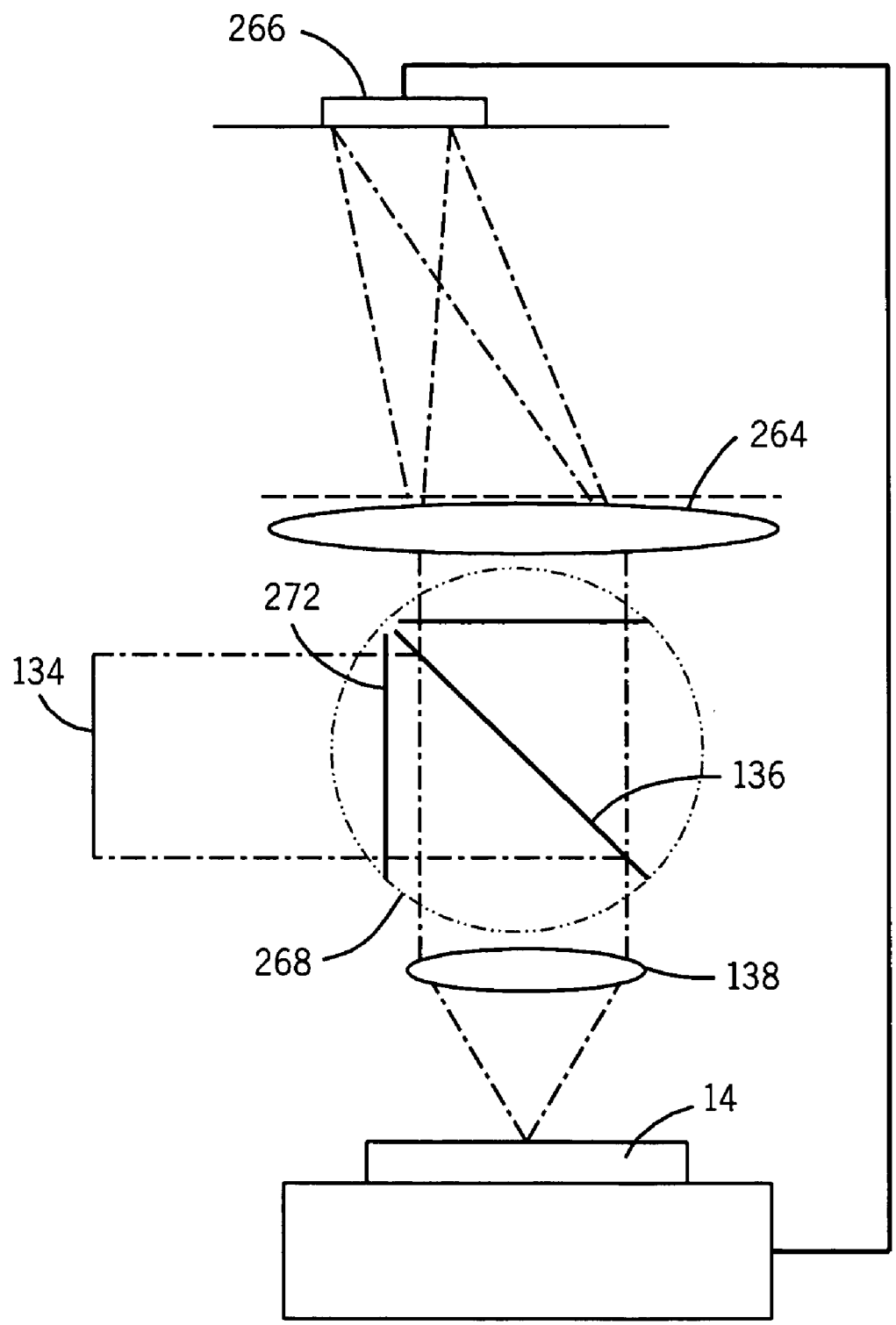
Figure 26:
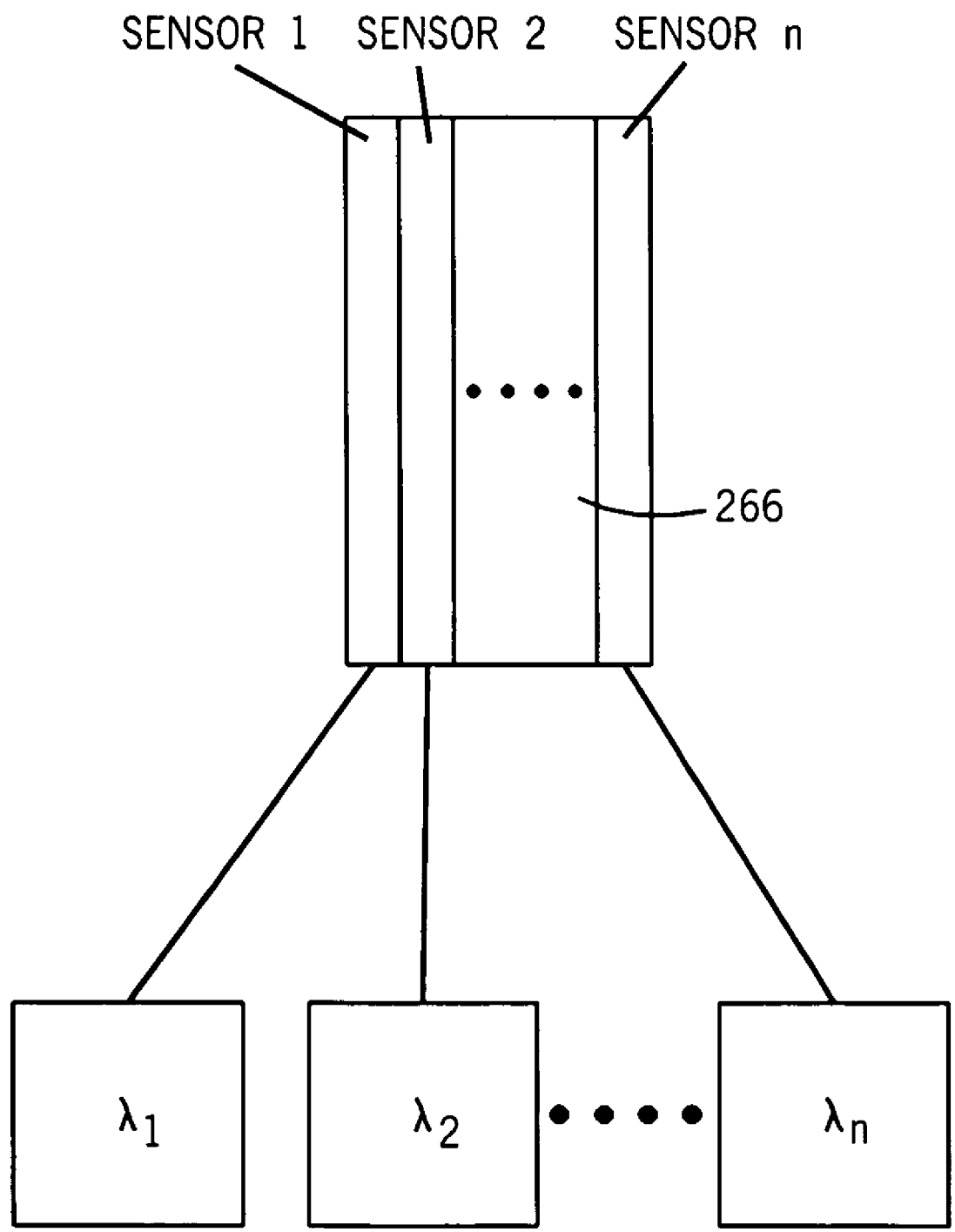
Figure 27:
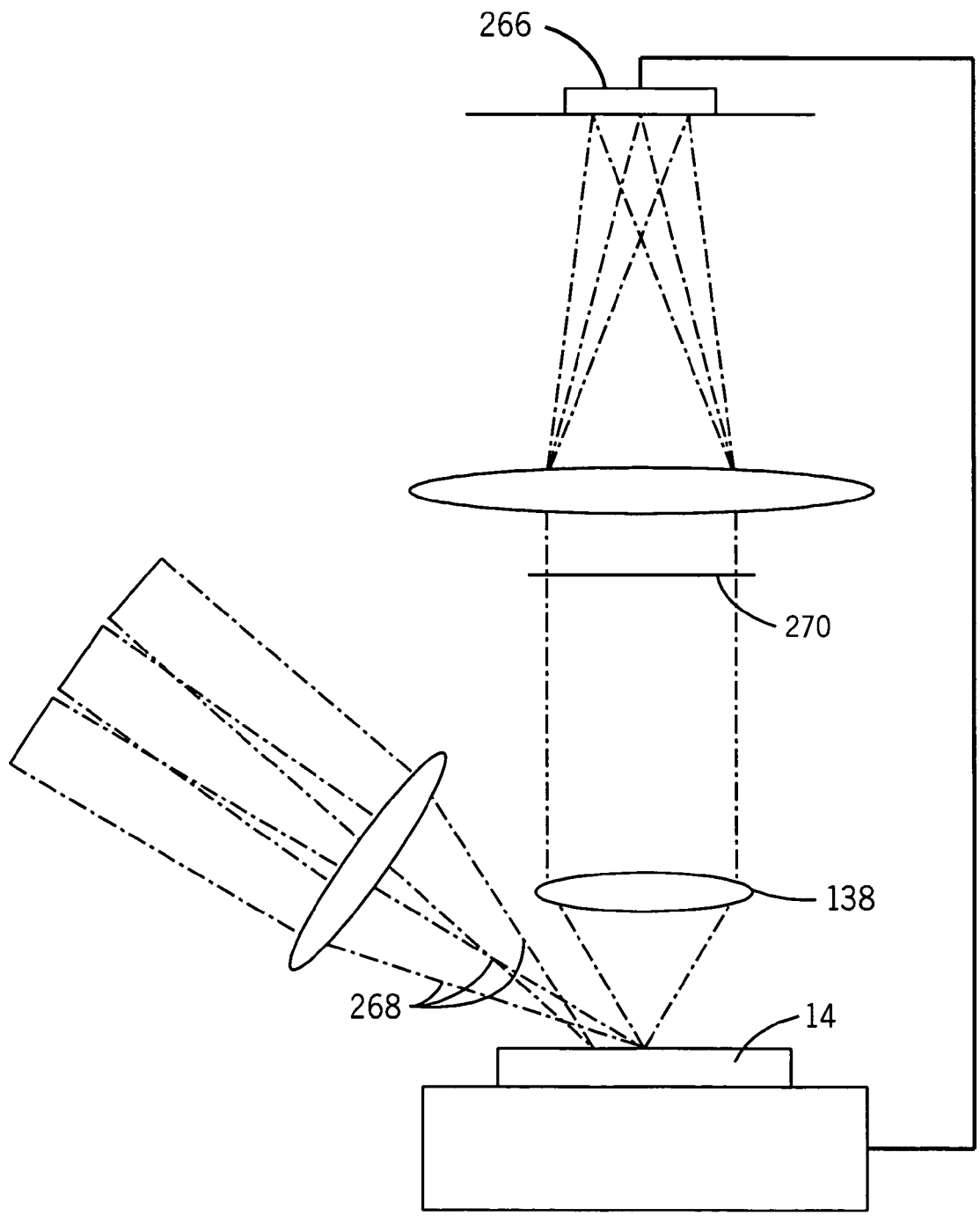
Figure 28:
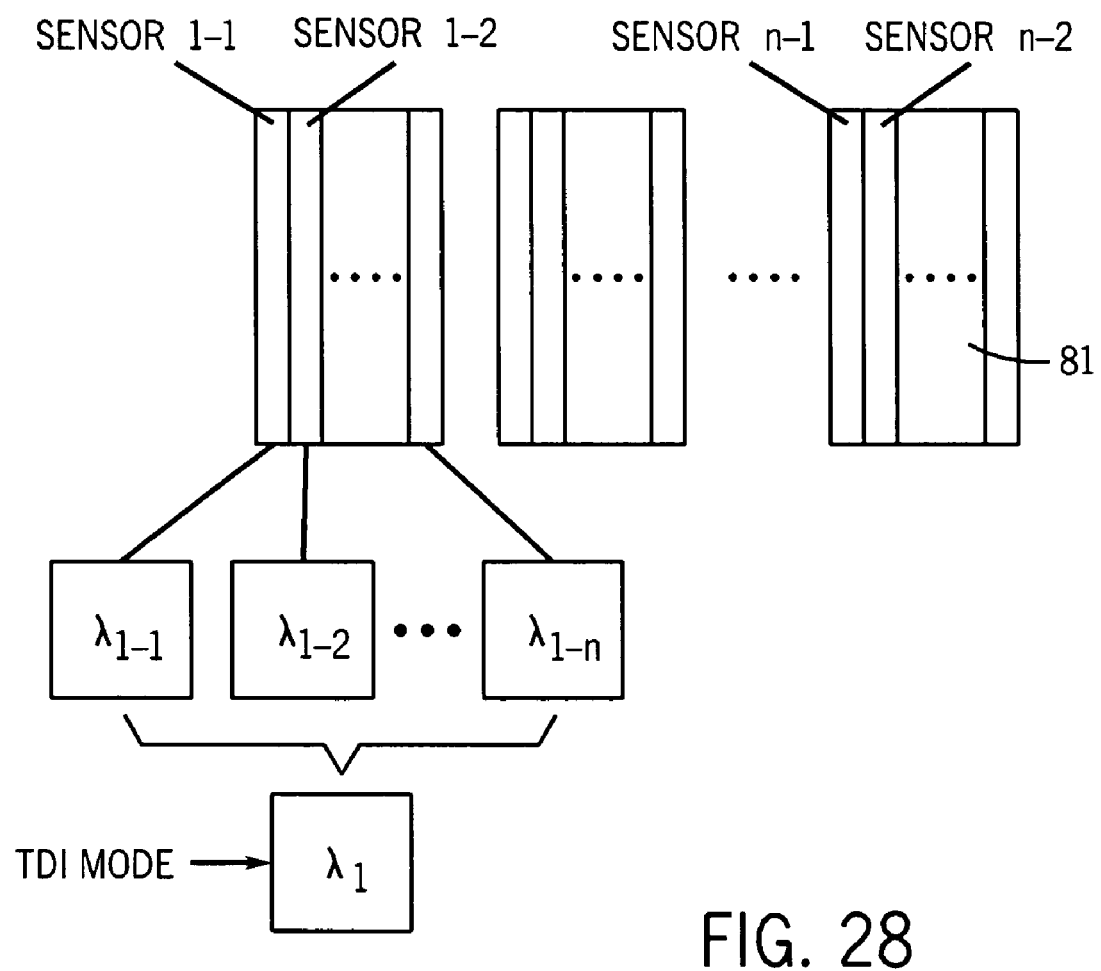
Figure 29:
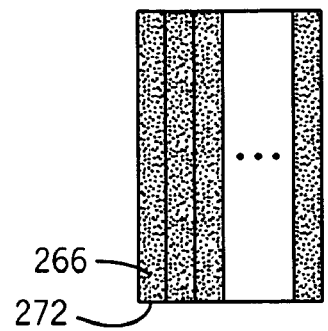
Figure 30A:
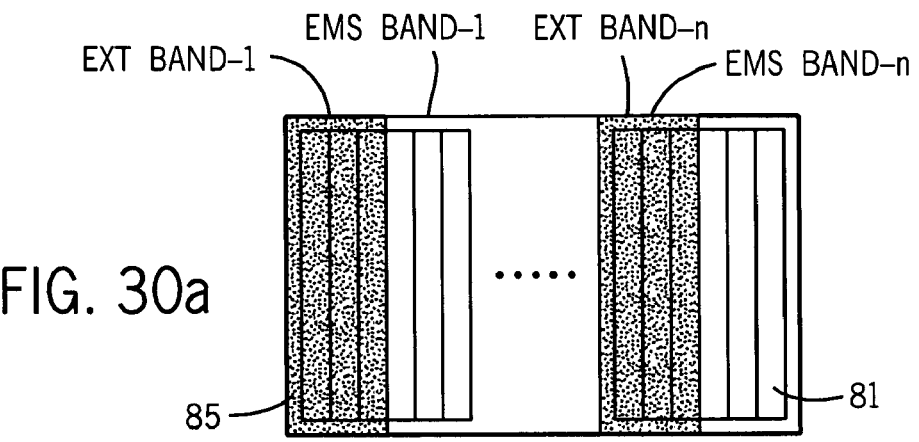
Figure 30B:
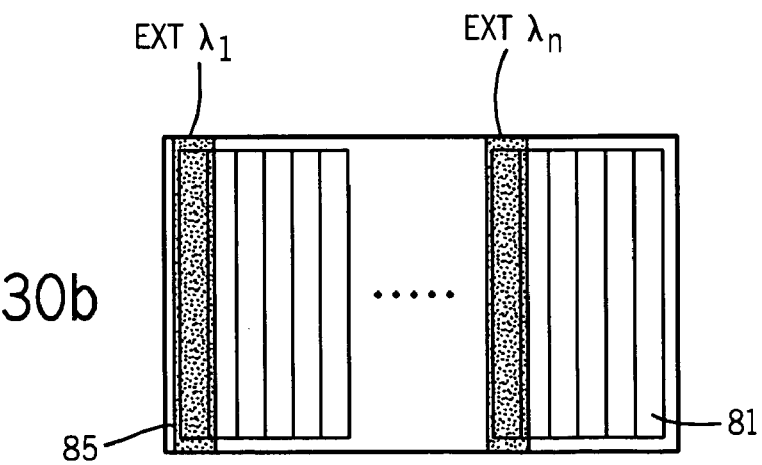

FIGS. 24(a)-(c) are diagrams showing the projection of a laser spot on a line scan camera and binning and TDI implementations in accordance with certain aspects of the invention;

FIG. 25 is a diagrammatical view of an image scanning system that is configured to conduct multi-spectral fluorescence imaging in accordance with aspects of the invention;

FIG. 26 is a block diagram of an exemplary line-scan imaging sensor for use with the system shown in FIG. 25;

FIG. 27 is a diagrammatical view of a further image scanning system that is configured to conduct multi-spectral fluorescence imaging;

FIG. 28 is a block diagram of an exemplary line-scan imaging sensor for use with the system shown in FIG. 27;

FIG. 29 is a block diagram of an exemplary line-scan imaging detector for use with the invention; and FIGS. 30(a)-(b) are block diagrams of other exemplary line-scan imaging detectors for use with the invention.

DETAILED DESCRIPTION

The present invention provides an image scanning system and architecture having rapid scan times while maintaining high resolution and image quality. These and other advantages result from configuring a detector array to achieve confocality in the scanning axis by restricting the scan-axis dimension of the detector array. As set forth in further detail below, an apparatus of the invention can be configured to achieve confocality in a single axis of a detector array such that confocality only occurs in that dimension.

The detector array can have rectangular dimensions such that the shorter dimension of the detector is in the scan-axis dimension. Imaging optics can be placed to direct a rectangular image of a sample region to the detector array such that the shorter dimension of the image is also in the scan-axis dimension. In this way, the detector array forms a virtual slit.

A virtual slit configuration provides several advantages over the use of a typical slit placed in front of a detector. For example, configuring a detector array as a virtual slit reduces the number of unused array elements compared to a configuration in which a detector array, having standard dimensions, is used with a slit. Reducing the number of unused elements increases efficiency of data acquisition and reduces image processing time. Furthermore, using a virtual slit allows both the detector and slit to be at the focal plane of the projection lens eliminating any focus compromise of either position or the requirement for a relay lens between the slit and detector.

A detector array configured to have a virtual slit is particularly useful when employed in an imaging apparatus that is further configured to direct a radiation line to a sample. The radiation line can have rectangular dimensions in which the shorter dimension is short enough to achieve confocality in a single axis corresponding to the shorter dimension of the detector array. Thus, confocality can be achieved for, excitation, detection or both. An instrument can be configured to limit excitation error in the confocal axis such that predominantly all of the excitation radiation is contained within a spot comparable with the resolution of the instrument.

An apparatus that includes a detector array forming a virtual slit can be configured to obtain an image of the sample at high resolution, for example, in the low micron to submicron range. In particular embodiments, an image can be obtained at a Rayleigh resolution between 0.2 and 10 micrometers. Furthermore, the ratio of the shorter of the two rectangular dimensions for the rectangular detector array and the product of the Rayleigh resolution of the imaging optics multiplied by the magnification of the imaging optics can be used to determine the size and dimensions of the virtual slit for achieving confocality in a single axis. If desired, the ratio of the shorter of two rectangular dimensions for a radiation line to the Rayleigh resolution of the imaging optics can be selected to achieve confocality in a single axis.

Accordingly, an imaging apparatus of the invention can be configured to have resolution along the length of the line perpendicular to the scan axis that is matched to the system resolution. For example in a CCD device, 4000 CCD elements can be used along the length of a 2 mm radiation line (the horizontal axis) resulting in a 0.5 μm pixel resolution at a sample. The number of CCD elements "n" in the direction perpendicular to the radiation line (the vertical axis) can be chosen to collect substantially all of the emitted radiation while reducing the amount of unwanted background radiation collected.

An imaging apparatus of the invention can be further configured such that all pixel elements in the vertical axis are collected in a common "bin" and read out as a single value. Advantages of the binning approach compared to a typical Time Delay Integration (TDI) design are that the readout rate can be reduced by a factor of "n", the system has confocality in one axis, and the tolerance of the synchronization timing of the readout with the y-stage movement can be reduced. It will be understood that a TDI design can be configured to have a virtual slit by limiting the number of vertical pixels. An additional advantage over system designs where n=1 are that the collection efficiency of the system can be increased and the sensitivity to small optical alignment drifts can be decreased.

Figure 1:
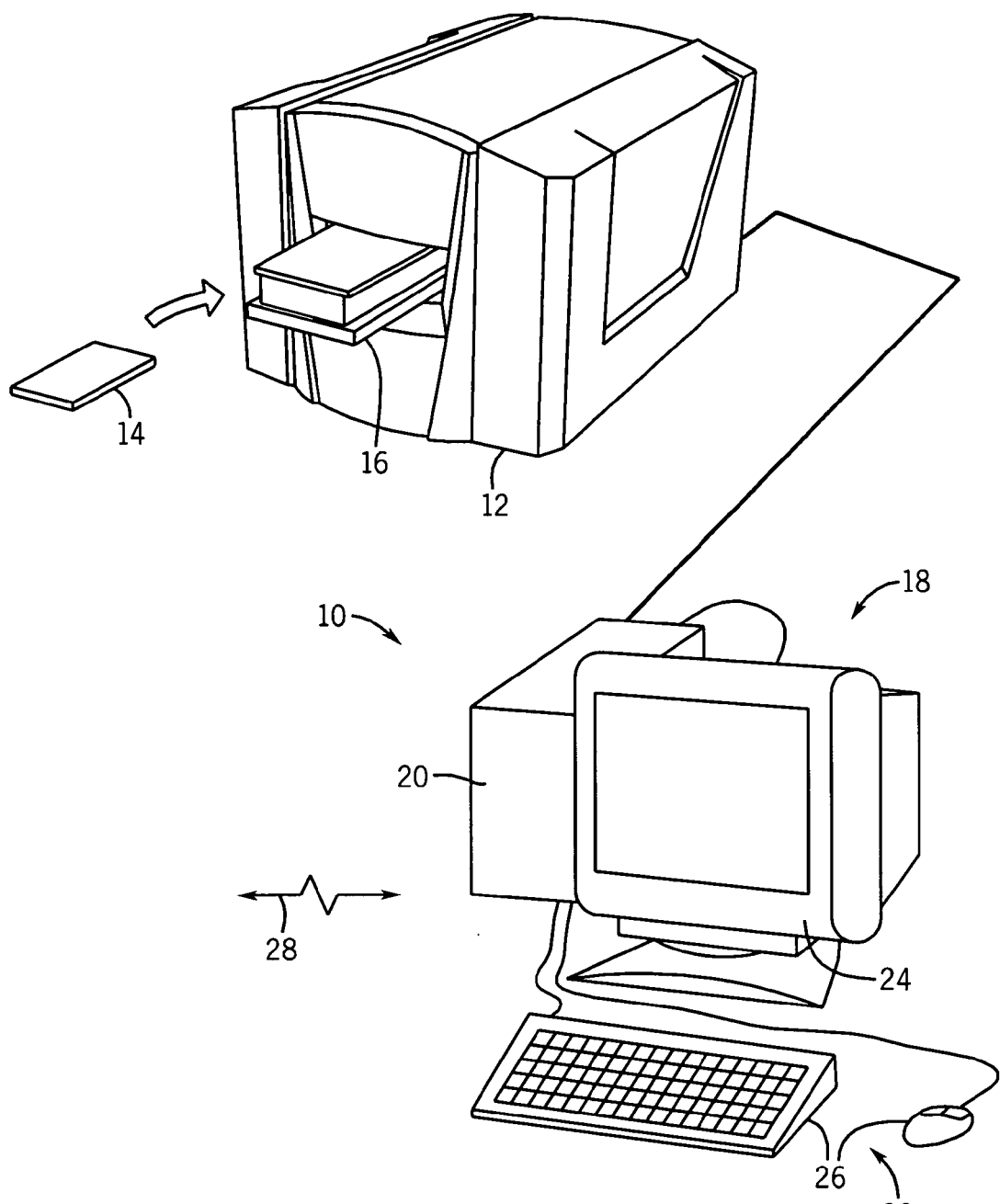
FIG. 1 is a diagrammatical overview of a microarray scanning system for confocal line scanning of a microarray in accordance with aspects of the present technique.

Turning now to the drawings, and referring first to FIG. 1, an imaging system 10 is illustrated diagrammatically as including a scanner 12 in which a sample or microarray 14 may be inserted for imaging purposes. As described more fully below, the microarray 14 includes a substrate or support on which an array of sites is formed. Each site including an attached molecular fragment, such as a gene or gene fragment, which may have attached thereto a molecule, which may be a complementary molecule in the case of DNA or RNA probes, from a specific sample. In present embodiments, many thousands of such sites may be provided in rows or a grid pattern in portions or segments on the microarray. The microarray itself may be formed by various technologies, including, as in a present embodiment, microbeads. Other microarrays which may be imaged in accordance with the present techniques may include microarrays formed by photolithography, and other processes known or developed in the art.

The scanner 12 will include optics described in greater detail below for confocal line scanning of the sites on microarray 14. In the illustrated embodiment, the scanner is a table-top device having a sample tray 16 in which the microarray, or a plurality of microarrays may be positioned. The tray may be configured to advance the microarray 14 into a scanning position, and subsequently slowly move the microarray, as described below, to allow successive lines on the microarray to be irradiated, and return radiation or retrobeams caused by fluorescence of individual sites. The retrobeams are focused on a detector for imaging and analyzing the sites, also described below. In particular embodiments, multiple retrobeams can be focused to multiple different detectors. For example, a retrobeam of a first wavelength can be focused to a first detector and a retrobeam of a second retrobeam can be focused to a second detector, as set forth in further detail below.

Control signals for operation of the scanner 12 originate from a controller or workstation 18. The workstation 18 also includes software for receiving the imaging signals from the scanner 12. The imaging software of workstation 18 will typically be embodied in a general purpose or application-specific computer 20 which also controls and receives signals from interface components 22, which will typically include a monitor 24 and input devices 26. The imaging software operable in workstation 18 will preferably provide an intuitive interface for loading and initializing the scanner, for performing imaging scans on microarrays, and for saving the data. During the scanning process, the system 10 creates individual files for different wavelengths of radiation used to image the microarray, which may be referred to herein as red and green channels. These may be provided in a consolidated file. Data and associated images may then be saved in a convenient format, such as a conventional TIFF format, or any other suitable image data format or protocol. The workstation 18 may be coupled to other network components, including down-stream processing and application-specific software for higher-level and data analysis, such as via a network indicated generally by reference numeral 28 in FIG. 1.

Figure 2:
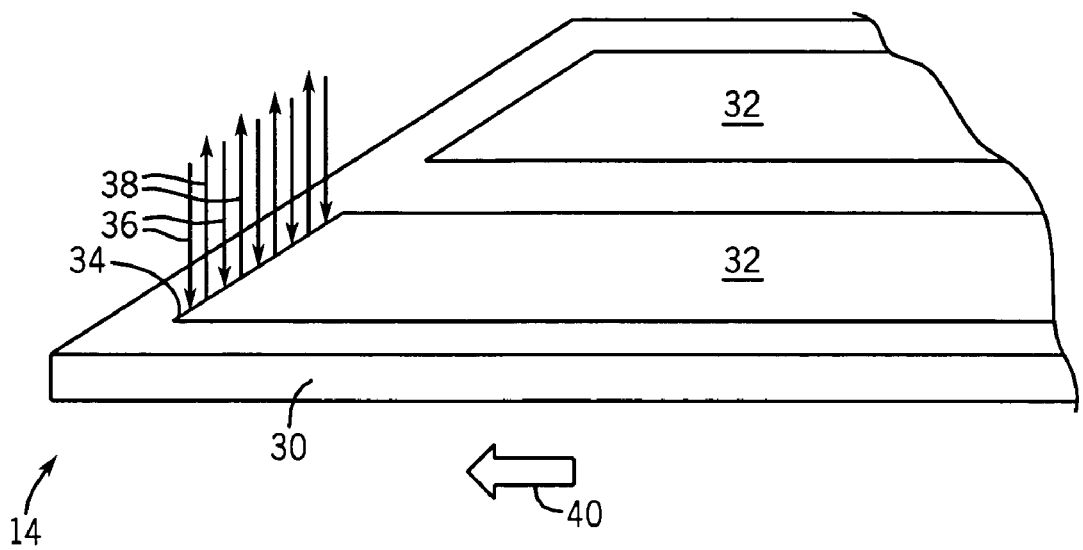
FIG. 2 is a diagrammatical perspective view of a portion of a microarray illustrating an exemplary manner in which a radiation line is directed toward regions of the microarray in which sites are located that are to be imaged.

As noted above, the microarray 14 will include a plurality of sites arranged in portions or regions of a substrate, for example, as indicated generally in FIG. 2. As shown in FIG. 2, the microarray 14 may include a support or substrate 30, which may be a glass, a plastic, a semiconductor, or any other convenient support such as those described elsewhere herein. On this support 30, one or more sample areas 32 are provided in which individual sites will be formed, each typically provided with a respective probe molecule used to test a sample. In a present invention, the sample area 32 is scanned for imaging purposes by a radiation line, indicated generally by reference numeral 34 in FIG. 2. The radiation line is formed by excitation radiation which is confocally directed along the line 34 to irradiate a plurality of sites simultaneously, as indicated generally by arrows 36 in FIG. 2. The individual sites at which target molecules (e.g., genetic fragments) will have bound are thereby caused to fluoresce due to the presence of dyes indicative of an interaction of a target with the site, returning radiation as indicated by lines 38 in FIG. 2. As described below, this returned radiation, or retrobeam, will be confocally directed toward an imaging detector where an image will be made of the line for further processing and analysis. To permit the sites to be successively imaged, then, the entire microarray may be displaced slowly as indicated generally by reference numeral 40. The line 34 along which the sites are irradiated will thereby generally progress along successive parallel locations on the microarray as the microarray is displaced.

Figure 3:
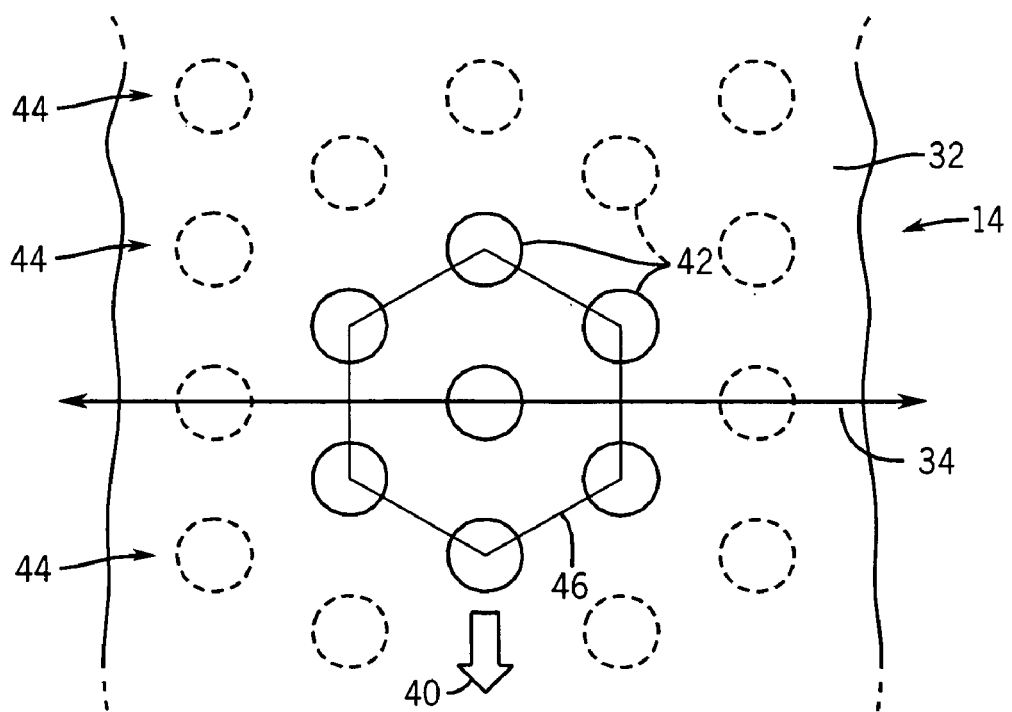
FIG. 3 is a more detailed diagrammatical representation of a portion of a microarray that is illuminated by a confocal radiation line to image the sites on the microarray in accordance with the present technique.

An exemplary portion of a microarray imaged in accordance with such confocal line scanning is illustrated in FIG. 3. Again, reference numeral 14 refers to the microarray, while reference numeral 32 refers to one of the sample areas in which individual sites 42 are disposed. In the illustrated embodiment, the sites are provided in a generally hexagonal pattern. Scanning by line 34 progresses through successive lines 44 of sites 42. As described in greater detail below, while the present confocal line scanning approach may be used with different layouts or grid patterns of sites on the micorarray, a hexagonal pattern is particularly useful with confocal line scanning insomuch as it provides for a reduced probability of crosstalk due to the placement and spacing between the sites or site edges. The hexagonal packing, designated generally by reference numeral 46 in FIG. 3, is believed to provide an optimal degree of accuracy due to such crosstalk reduction, balanced with a superior packing density of the sites.

As described below, and as also illustrated in FIG. 3, as the microarray 14 is advanced as indicated by reference numeral 40, the confocal radiation line 34 irradiates a plurality of sites located along the line. The line is wider, in a horizontal direction shown in FIG. 3 than it is high. Thus, the line may irradiate adjacent sites in a line or row of sites without irradiating sites in adjacent lines. In a present embodiment, however, the radiation line 34 is sufficiently thin, at the level of the sites, or of a sufficient vertical height in the arrangement illustrated in FIG. 3 to permit it to illuminate less than the entire area occupied by the sites. In a presently contemplated embodiment, the radiation line 34 is, for example, 2 mm in length (horizontal dimension) and less than 3 mm in height (vertical dimension). Thus, the software provided for imaging, mentioned above, may employ techniques such as time delay imaging, in which the readout from the detector described below is shifted with movement of the sample to provide more accurate representations of the individual sites in each row or line.

For purposes of explanation, several aspects of the invention have been exemplified with regard to moving a microarray past a radiation line. It will be understood that embodiments in which the radiation line is moved in addition to or alternatively to moving the microarray can also be used. Thus, line-scanning can be carried out by relative displacement of a radiation line and/or microarray relative to each other. A portion of the sample excited by the radiation line can form a rectangular image on the detector array (described below).

Figure 4:
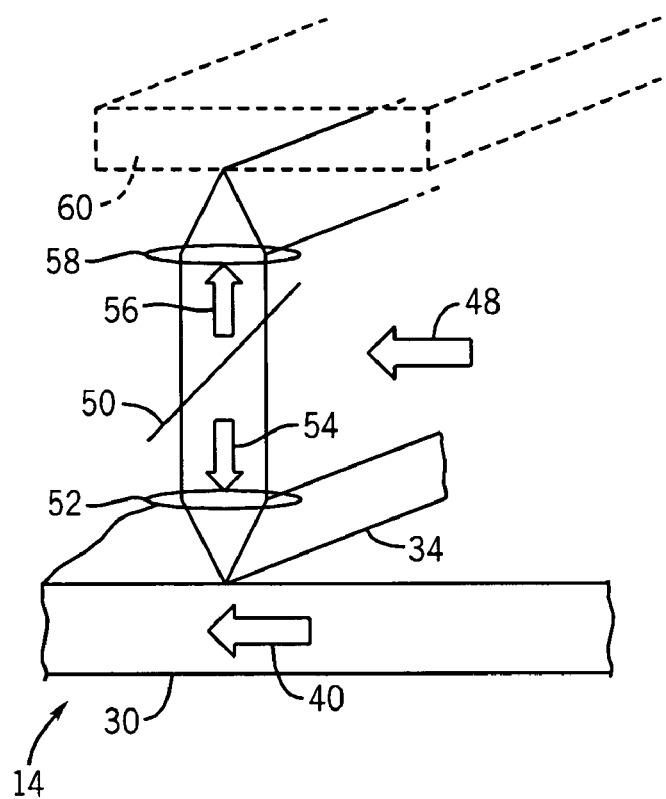
FIG. 4 is a diagrammatical perspective view of a combined radiation line directed toward a surface of a microarray to confocally irradiate sites on the array, and to confocally return radiation to a detector in accordance with aspects of the present technique.

FIG. 4 is a further diagrammatical representation of the present confocal line scanning approach to imaging the microarray 14. As indicated above, the microarray is radiated along a line 34 as the support 30 is slowly moved as indicated by reference numeral 40. As illustrated in FIG. 4, the line 34 is formed by radiation from a source 48 which is directed towards directing optics 50 and therefrom to focusing optics 52. As described more fully below, the radiation source 48 will be a beam with a linear cross section or a radiation line including a plurality of wavelengths of light used to cause fluorescence at correspondingly different wavelengths from the sample, depending upon the particular dyes used. The focusing optics 52 will then confocally direct the radiation line toward the substrate 30 to irradiate the sites as described above along line 34. It should be noted that the sites may be provided at the surface of the substrate 30 or slightly below the surface (e.g., below a protective film or layer). The confocal irradiation along line 34 will essentially focus the radiation toward the sites themselves at whatever level they are found in the microarray.

The excitation path 54, in the present embodiment, is coplanar with a retrobeam path 56 for radiation returned from the sample by fluorescence of dyes associated with molecules attached to probes at the individual microarray sites. The returned radiation is again focused by focusing optics 58 such that it impacts a detector 60 to create imaging signals used to reconstruct an image of the microarray, and of individual sites on the microarray. Specific embodiments for creating the radiation beam, directing the beam to the microarray, and for detecting returned radiation are described in greater detail below.

Figure 5:
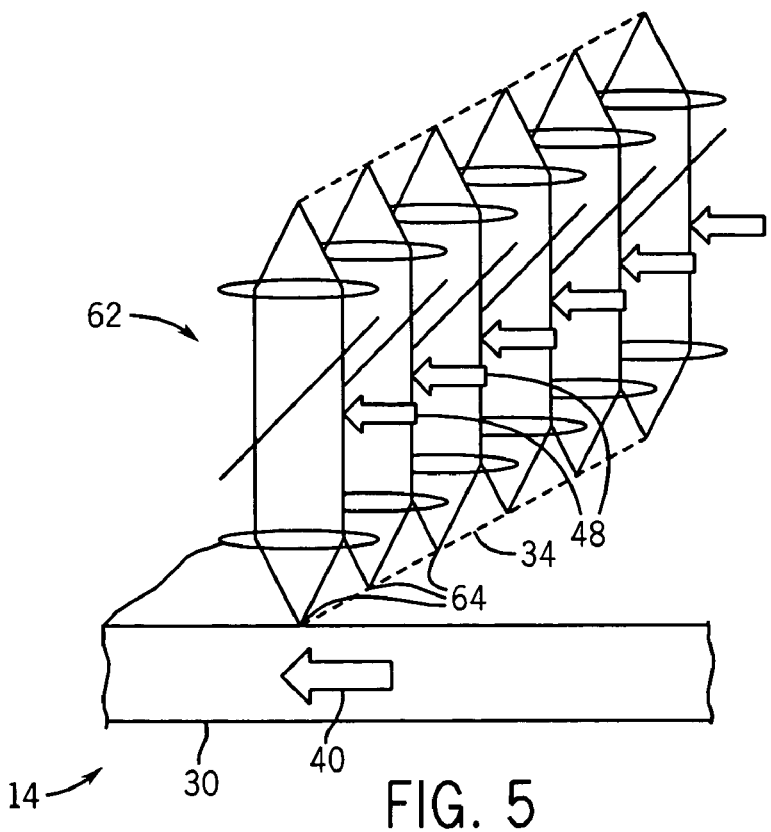
FIG. 5 is a similar diagrammatical perspective view illustrating a series of confocally directed beams of radiation along a line for similarly irradiating sites of a microarray in accordance with the present technique.

It should be noted that, as illustrated generally in FIG. 5, the radiation line used to image the sites simultaneously, in accordance with the present invention, may be a continuous or discontinuous line. FIG. 5 represents, diagrammatically, a discontinuous line made up of a plurality of confocally directed beams of light which nevertheless irradiate a plurality of points along a line 34. In the embodiment illustrated in FIG. 5, discontinuous beams 62 are created from separate but adjacent radiation sources 48. These beams, as before, are confocally directed toward the microarray and irradiate adjacent spots 64 along the microarray in a line 34. As with the continuous confocal line scanning described above, the microarray will typically be advanced slowly as indicated by arrow 40 to irradiate successive lines along the microarray, and thereby successive rows or lines of sites.

Typically, the invention is used to excite and detect a line simultaneously. In some embodiments, line confocal point scanning can be used such that the optical system directs an excitation point or spot across a sample by scanning the excitation beam through an objective lens. The detection system images the emission from the excited point on the detector without "descanning" the retrobeam. This occurs since the retrobeam is collected by the objective lens and is split off the excitation beam optical path before returning back through the scan means. Therefore the retrobeam will appear on the detector at different points depending on the field angle of the original excitation spot in the objective lens. The image of the excitation point, at the detector, will appear in the shape of a line as the excitation point is scanned across the sample. This architecture is useful, for example, if the scan means cannot for some reason accept the retrobeam from the sample. Examples are holographic and acoustic optic scan means that are able to scan a beam at very high speeds but utilize diffraction to create the scan. Therefore the scan properties are a function of wavelength. The retrobeam in fluorescence is at a different wavelength from the excitation beam.

Figure 6:
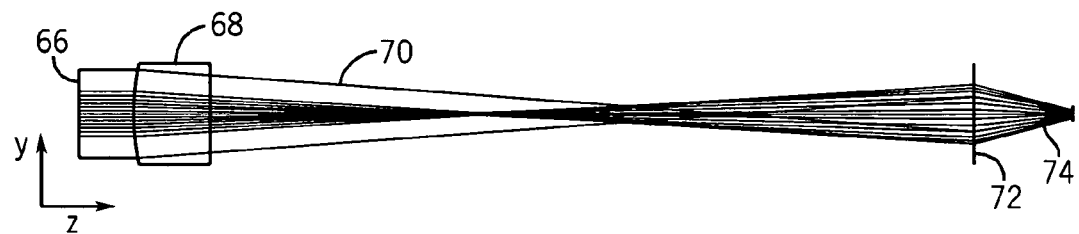
FIG. 6 is a diagrammatical side view of a technique for converting output of a laser to a radiation line for confocal line scanning of a microarray.
Figure 7:
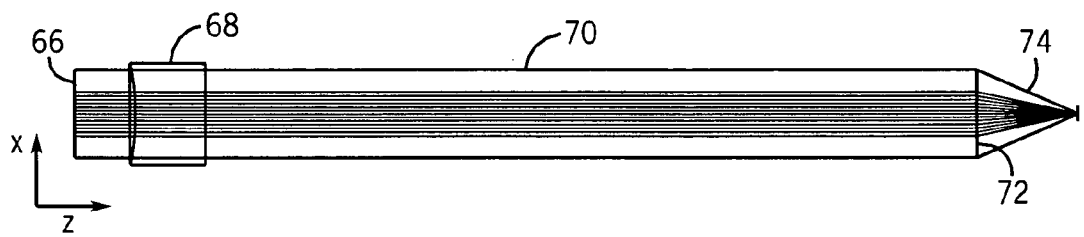
FIG. 7 is a similar, top view of the conversion of the output of a laser to a radiation line for use in the present confocal line scanning technique.

FIGS. 6 and 7 illustrate an exemplary linearization of an input laser beam for confocal line scanning of a microarray in accordance with a presently contemplated embodiment. FIG. 6 represents what may be considered an elevational view of the conversion or linearization of the input beam, while FIG. 7 may be considered to illustrate a top plan view, although these orientations are understandably interchangeable, depending upon the orientation of the line and microarray to be scanned, as described below. As shown in FIG. 6, an input beam 66 from a laser (not shown) will typically take the form of a circular Gaussian beam 66. An aspherical lens 68, such as a Powell lens converts the input beam to a line 70 of radiation which is directed toward an objective lens 72. As illustrated in the top view of FIG. 7, the aspherical lens 68 effectively produces a generally flat radiation line which is further converted to a confocally concentrated beam 74 by the objective lens 72.

Figure 8:
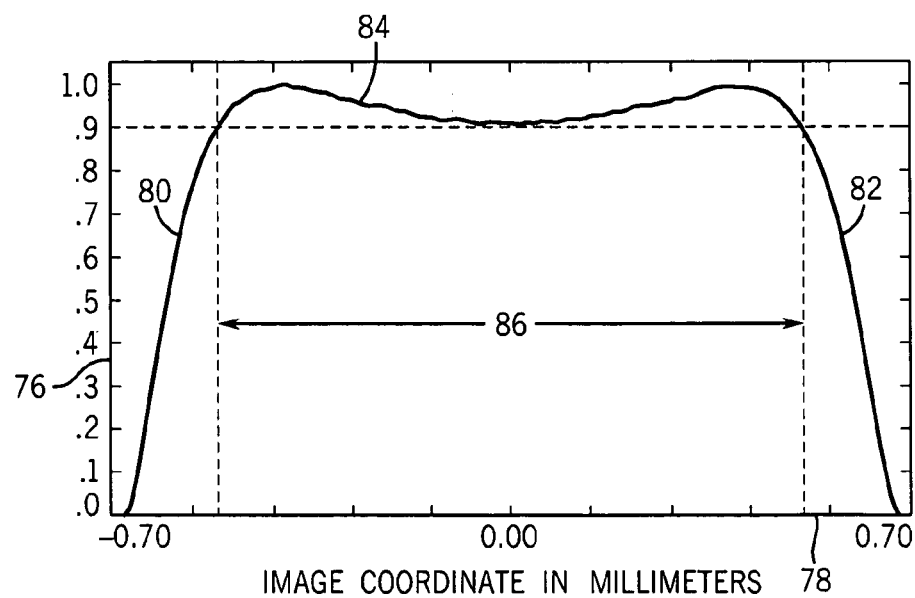
FIG. 8 is a graphical representation of an intensity profile for a radiation line produced by the arrangements of FIGS. 6 and 7.

As illustrated in FIG. 8, the arrangement shown in FIGS. 6 and 7 produces a linear region of radiation which can be used to simultaneously irradiate a number of sites on the microarray. FIG. 8 is a graphical representation of the simulated illumination along a radiation line produced by an aspherical lens as described with reference to FIGS. 6 and 7. The relative illumination of the beam is indicated by vertical axis 76, while the image coordinate in millimeters is represented by the horizontal axis 78. In the illustrated embodiment, the illumination intensity rises rapidly near an edge of the aspherical lens, as indicated by reference numeral 80 and drops rapidly near an opposite edge, as indicated by reference numeral 82. Between the edges a useful segment of radiation 84 has a substantially constant relative illumination level. In a present embodiment, the useful width 86 of the radiation line is used to irradiate lines or rows of sites on the microarray simultaneously. The simulation illustrated in FIG. 8, for example, provided a useful scanning length 86 of approximately 1.024 millimeters, although a number of factors, including the optics involved may provide for other useful radiation line lengths.

As will be appreciated by those skilled in the art, for imaging at a plurality of wavelengths, a confocal line scanning fluorescence imaging system in accordance with the present technique will provide for lines of multiple wavelengths with the diffraction-limited width and uniform distribution along a length to irradiate sample sites and thereby to excite multiple fluorescent dyes. The line generator approach illustrated in FIGS. 6, 7 and 8 provide an exemplary mechanism for such linearization of irradiating, multiple wavelength light. The provision of multiple wavelengths in the radiation line will be described in greater detail below. Effectively, the arrangement illustrated in FIG. 6, 7 and 8 fan a collimated input beam in one dimension and maintain the beam collimated in a perpendicular dimension. The beam is then focused by the objective lens 72 to a diffraction-limited line on a focal plane of the lens.

Based upon the sag of the aspherical lens, a collimated pure Gaussian input beam with a defined beam diameter is preferred to generate a line of uniform distribution. A presently contemplated technique for obtaining a beam with an almost pure Gaussian distribution is the use of a single mode fiber or fiber cable to provide input to the aspherical lens.

Figure 9:
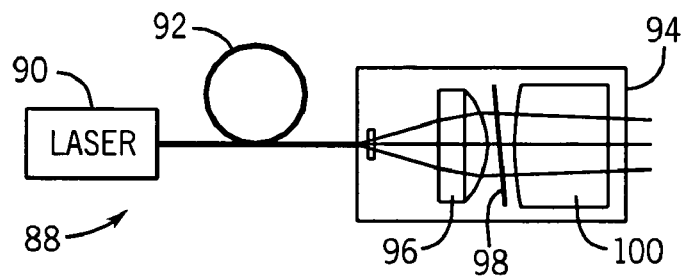
FIG. 9 is a diagrammatical representation of a first exemplary configuration for a modular arrangement used in converting output of a laser to a radiation line for confocal line scanning in accordance with the invention.

Several arrangements may be foreseen for use of such a single mode fiber or fiber cable. FIG. 9 illustrates a first exemplary embodiment in which a linear radiation source 88 includes a laser 90 coupled to a single mode fiber pigtail 92 and therethrough to a line generator module 94. The objective lens downstream of the aspherical lens is omitted from the illustration in FIG. 9. The generated line profile is not only sensitive to the input beam profile but also sensitive to input beam diameter, collimation characteristics and centering of the beam to the aspherical lens. That is, the aspherical lens may be designed for a defined input beam diameter, and the assembly, particularly the components of the line generator module 94, is aligned to achieve the design performance.

In the illustrated embodiment, the line generator 94 includes several optical components which are pre-aligned in a modularized assembly to facilitate both their quality control and packaging in the scanner. In particular, line generator modular 94 may include a collimator 96 that collimates, the input beam from the single mode fiber 92 and directs the collimated beam to an aspherical lens 100. A laser line filter 98 may also be employed, particularly for applications of fluorescence imaging, to reduce background noise. The illustration of FIG. 9 may provide for pre-assembling or terminating the single mode fiber 92 on both ends, that is, at the laser 90 and at the line generator module 94.

Figure 10:
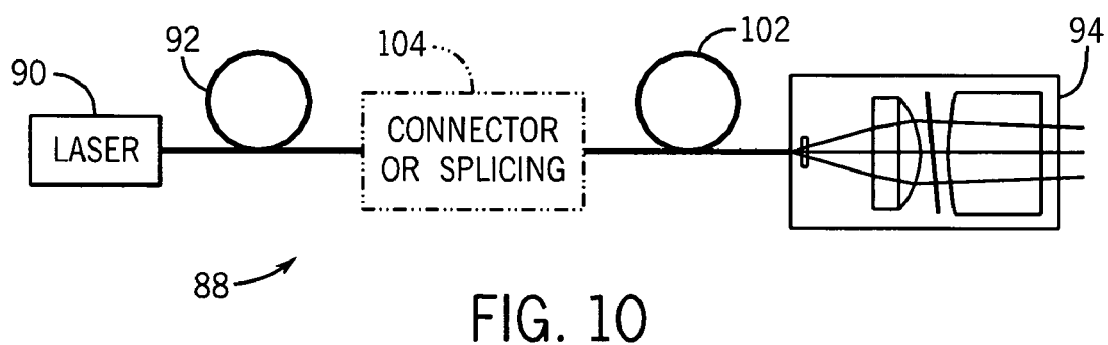
FIG. 10 is an alternative arrangement for conversion of a laser output to a radiation line in accordance with the present invention.
Figure 11:
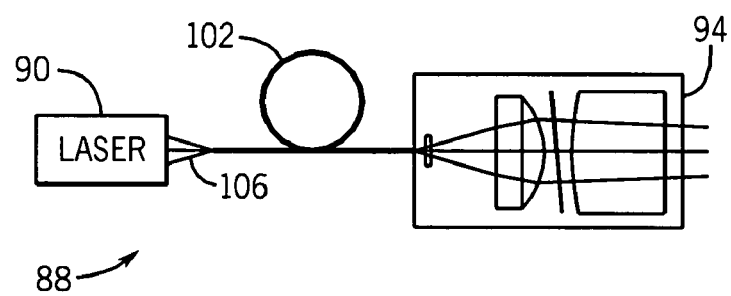
FIG. 11 is a further alternative arrangement for converting laser output to a radiation line in accordance with the invention.

Alternatively, the linear radiation source 88 may provide for splicing a pair of fiber pigtails as illustrated generally in FIG. 10. In the embodiment of FIG. 10, the fiber pigtail 92 is pre-coupled to the laser 90, while a second fiber pigtail 102 is pre-coupled to the line generator module 94. The two fibers may then be connected or spliced at an intermediate point as indicated generally by reference numeral 104.

In a further alternative configuration, illustrated in FIG. 1, a single fiber pigtail 102 may again be used, which may be pre-assembled with the line generator module 94. In this embodiment, however, the laser 90 provides input to the fiber pigtail 92 by active coupling, as indicated by reference numeral 106.

Figure 12:
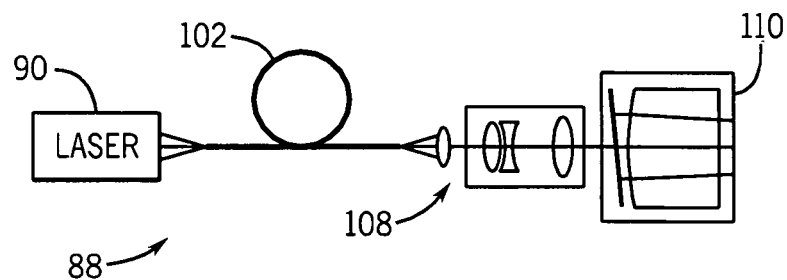
FIG. 12 is yet another alternative configuration for converting laser output to align a radiation.

In a further alternative configuration, illustrated generally in FIG. 12, a fiber pigtail 102 may be pre-assembled with laser 90. Rather than providing a collimator in the line generator module 94 as described above, a variable beam expander 108 may be employed for providing input to a modified module 110 which includes an aspherical lens, as before. The embodiment of FIG. 12 may require that the input beam diameter match the desired diameter by virtue of the variable beam expander 108.

Figure 13:
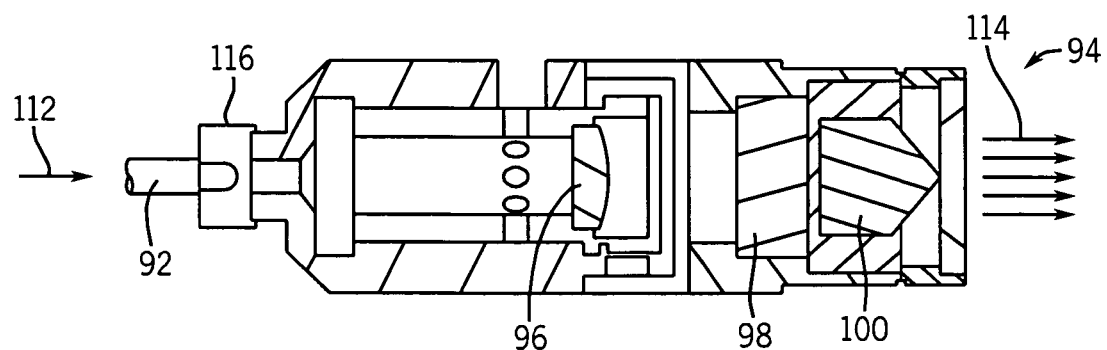
FIG. 13 is a sectional view of an exemplary line generator module suitable for use in accordance with the invention.

An exemplary line generator module 94 is illustrated generally in FIG. 13. As indicated above, and as shown in the physical implementation of FIG. 13, the module 94 may receive an input beam, designated generally by reference numeral 112, via a single mode fiber 92. An output radiation line 114 is emitted by the module. In the illustrated embodiment, a fiber optic connector 116 serves to join the single mode fiber 92 to the input side of the module 94. Therefrom, the beam propagates through collimator 96, laser line filter 98 (where provided), and aspherical lens 100. Again, the modularization of the optical components used to convert the output of the laser to a radiation line is favored insomuch as it facilitates assembly of the overall system, alignment of the optics, and later servicing and replacement of the optical components, if needed.

As indicated above, in certain contemplated embodiments, the radiation source is a laser. Other useful radiation sources might include, for example, a lamp such as an arc lamp, quartz halogen lamp and light emitting diodes. Any of a variety of other radiation sources can be used as desired for exciting a sample at a particular wavelength. As desired for a particular application, the radiation source can generate radiation at various wavelengths including, for example, a wavelength in the UV, VIS or IR range. For example, an apparatus of the invention can include a laser that generates light at 405 nm, 488 nm, 532 nm or 633 nm.

Moreover as noted below, the system can include more than one radiation source. The multiple radiation sources can be lasers each capable of generating radiation at different wavelengths. The use of multiple radiation sources that generate radiation at different wavelengths can be useful, for example, in applications wherein a sample includes one or more fluorophores that produce different emission signals when excited at different wavelengths. Different emission signals can be collected simultaneously, for example, using multiple detection arms as set forth below in further detail. Alternatively or additionally, different emission signals can be collected sequentially following sequential excitation at different wavelengths.

As noted above, certain embodiments of the invention may further include an expander positioned to receive excitation radiation from a radiation source and to send an expanded beam of the radiation to a line generator. In particular embodiments, the diameter of the excitation beam generated by the radiation source is approximately 1 mm in diameter. A first expander is capable of expanding the diameter of the beam. For example, according to one embodiment, the expander expands the excitation beam to a diameter of 4 mm. Other useful beam expanders can bring the diameter of a radiation beam to at least about 0.5 mm, 1 mm, 2 mm, 5 mm, 10 mm, 15 mm, 20 mm or more.

As also discussed above a line generator useful in the invention can include a diffractive element configured to generate a diffraction-limited line with uniform intensity distribution. For example a cylindrical micro-lens array and a condenser can be used. The cylindrical micro-lens array can be configured to focus excitation radiation onto the front focal plane of the condenser to generate a diffraction-limited line with uniform intensity distribution. A further example of a line generator is a one-dimensional diffuser having an angular uniformity and a condenser, wherein the one-dimensional diffuser is placed at the front focal plane of the condenser to generate a diffraction-limited line with uniform intensity distribution. If desired, the line generator can further include an aspheric refractive lens to generate a diffraction-limited line with uniform intensity distribution. An exemplary aspheric refractive lens is a Powell lens.

In a particular embodiment, the line generator can be configured to receive an input excitation beam having a diameter of 4 mm to obtain a fan angle of 6 degrees. Other useful configurations include, but are not limited to, those that receive an input excitation beam having a diameter of at most about 0.1 to 50 mm. A line generator can obtain a fan angle of at least about 0.1° to at most about 80°, full width. The beam diameter and fan angle can be selected to achieve a desired shape for a radiation line. Generally, the width of the radiation line depends upon beam diameter such that a larger beam diameter provides a wider radiation line in the vertical dimension and the length of the radiation line depends on the fan angle such that a larger fan angle provides a longer radiation line in the horizontal dimension. Typically, the line should appear to originate at the pupil of the objective, however this is not a requirement.

As set forth above, any of a variety of optical elements capable of generating a line can be placed in the optical path between a radiation source and a sample region to be irradiated. For example, an arc lamp focused on a slit and then collimated can be used to generate a line. A further example is an edge emitting diode laser having an anamorphic beam which generates a line when focused. It will be understood that a radiation source used to irradiate a sample region can itself be capable of generating a line. Thus, a radiation source useful in the invention can include a line generator.

Any of a variety of methods and apparatus including, but not limited to those exemplified above, can be used to direct a radiation line to a sample region. The dimensions of the radiation line can be selected to achieve confocality in a single axis of a rectangular detector array. More specifically, the vertical dimension of the radiation line can be short enough to achieve confocality in the vertical dimension of the rectangular detector array.

A line generator of the invention is typically configured to produce a radiation line having a shape at a sample region that is rectangular or oblong. Exemplary shapes include, but are not limited to, a rectangular, elliptical, or oval shape. A line generator can be configured to produce a radiation line having one or more of the properties set forth below.

A radiation line that contacts a sample region can have a ratio of the $1/e^2$ width of the vertical dimension for the radiation line to the quotient of the vertical dimension for the rectangular detector array divided by the magnification of the imaging optics that results in confocality in one dimension. For example, the ratio can be at least about 0.5, 1, 1.5, 2, 3 or higher. An apparatus of the invention can be configured to have an upper end for the ratio that is at most about 2, 1.5, 1, 0.5 or lower. The ratio can be outside or inside the above ranges as desired including, for example, being in the range of 0.5 to 3.

A radiation line that contacts a sample region can have a ratio of the vertical dimension for the radiation line to the quotient of the vertical dimension for the rectangular detector array divided by the magnification of the imaging optics that results in confocality in one dimension. For example, the ratio can be at least about 0.1, 0.5, 1, 5, 10 or higher. The upper end of the ratio can be at most about 10, 5, 1, 0.5, 0.1 or lower. The ratio can be outside or inside the above ranges as desired including, for example, being in the range of 0.1 to 10.

Furthermore, the ratio of the vertical dimension for the radiation line to the Rayleigh resolution of the imaging optics can be at least about 0.1, 0.5 1, 5, 10 or higher. The upper end of the ratio can be at most about 10, 5, 1, 0.5, 0.1 or lower. The ratio can be outside or inside the above ranges as desired including, for example, being in the range of 0.1 to 10.

Although the invention is exemplified herein with regard to embodiments in which a sample region is contacted with a radiation line, it will be understood that the radiation that contacts a sample region can have other shapes including, for example, a square or circle.

As described below, an apparatus of the invention can include an objective positioned to receive radiation therethrough to illuminate a sample region. The objective can be further positioned to collect radiation emanating from a sample region and direct it to a detector array. Optionally, the apparatus can include a second expander positioned to receive the excitation radiation from the line generator and send an expanded beam of the radiation to the objective. The second expander can be further configured to decrease the field angle of the radiation line. For example, after the excitation beam passes through the line generator and/or a second expander, it may be directed to an objective by a beam splitter. In particular embodiments, the objective has an external pupil positioned to receive the radiation line therethrough to illuminate the sample region. Preferably, the beam splitter may be located near the entrance pupil of the objective lens. The beam splitter can be placed at an axial or lateral position relative to the objective. If desired, an objective can have a property of color correction, high numerical aperture, telecentricity, afocality at the backplane or a combination of such properties.

The beam splitter directs the radiation line to an objective. The objective can be a microscope objective. The objective may have a focal length of 20 mm. Accordingly, the objective may possess a numerical aperture of 0.366. Further, the objective may have a field angle of +/−3 degrees and an entrance pupil having a 16 mm diameter. Preferably, the objective is telecentric. Exemplary telecentric objective lenses useful in the invention include those that are described in U.S. Pat. No. 5,847,400, which is incorporated herein by reference.

Figure 14:
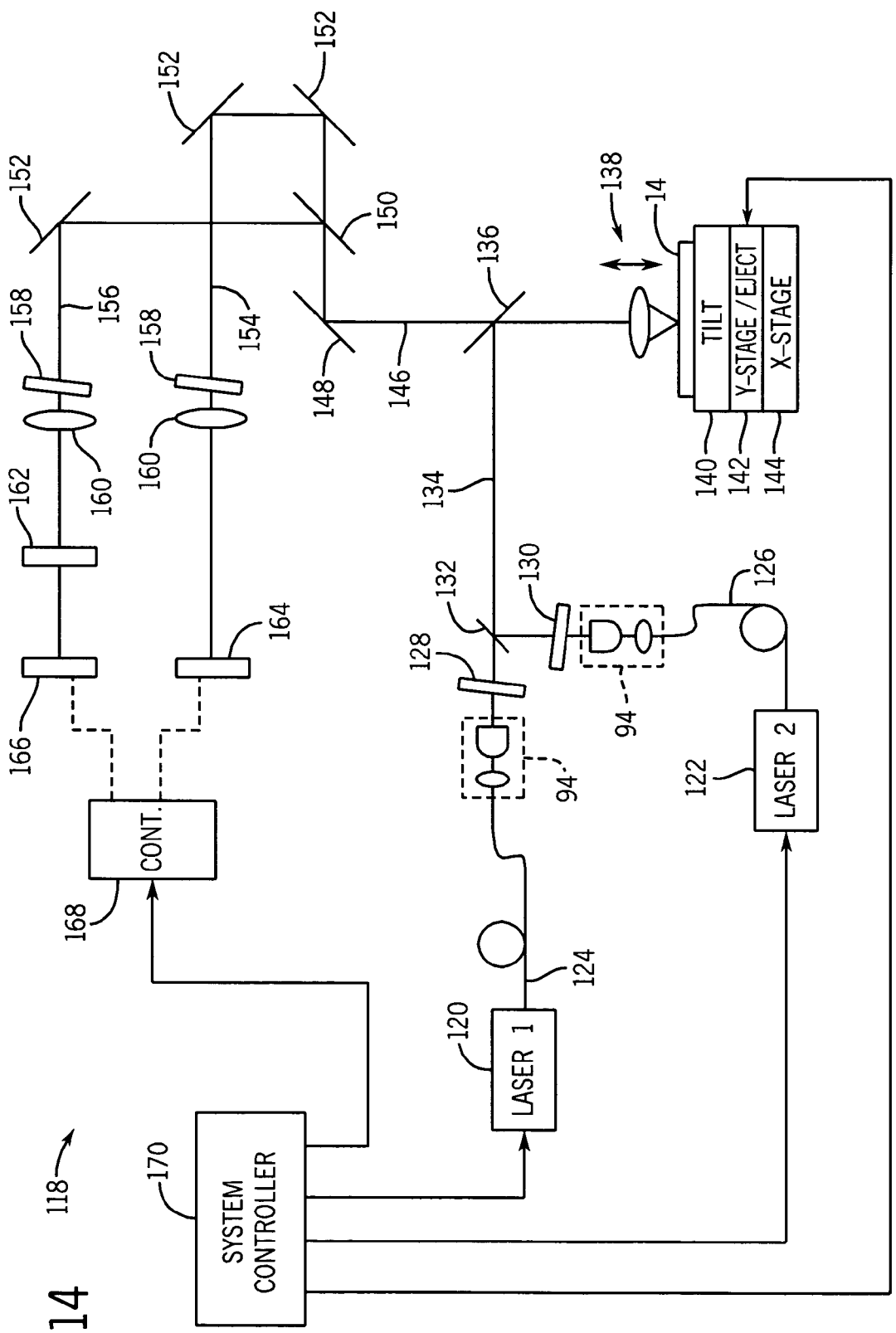
FIG. 14 is a diagrammatical overview for a scanning system that includes two laser beams, the output of which is combined for confocal line scanning of a microarray.

FIG. 14 illustrates an overall optical layout for the various components described above in a multiple wavelength scanner 1 18. The scanner 1 18 may include a plurality of laser light sources, with two such sources being illustrated in the embodiment of FIG. 14. These include a first laser 120 and a second laser 122. The first laser 120, in presently contemplated embodiments may be a 658 nm laser, a 750 nm laser, or a 635 nm laser, depending upon the desired application. The second laser 122 may be, for example, a 488 nm laser, a 594 nm laser, or a 532 nm laser. Other wavelength lasers may, of course, be used. In the present embodiment, the first laser 120 is a 635 nm laser when the second laser 122 is a 488 nm laser, or the first laser 120 is a 750 nm laser when the second laser 122 is a 594 nm laser, or the first laser 120 is a 658 nm laser when the second laser 122 is a 532 nm laser. The selection of the wavelength for each laser will depend, of course, upon the fluorescence properties of the dyes used in the microarray, although the wavelengths of the lasers used in unison for any particular imaging sequence will be distinct from one another to permit differentiation of the dyes at the various sites of the microarray.

Each laser 120 and 122 is coupled to a single mode fiber 124 and 126, respectively, as described above. Moreover, each fiber 124 and 126 feeds a line generator module 94 of the type described above. Downstream of each module 94, a filter wheel 128 and 130 may be provided. The filter wheels serve to block, pass or attenuate the light depending upon the desired function.

Output from each of the lasers 120 and 122 will be converted to a near pure Gaussian distribution by the respective single mode fibers 124 and 126, and the resulting beams will be converted to beams with linear cross-sections, also referred to as radiation lines, by the line generator modules 94. Downstream of the filter wheels 128 and 130, the two radiation lines will be combined by a beam combiner 132. The combined radiation line 134 will, then, comprise light at two different wavelengths for irradiating the microarray. The combined radiation line 134 is then directed to a dichroic beam splitter 136 which directs the beam toward focusing optics 138. The focusing optics 138 constitute a microscope objective that confocally directs and concentrates the radiation line along the line to the microarray 14 as described above. Although the invention is exemplified herein with regard to a combined radiation line that forms a single radiation line it will be understood that the two radiation lines can be combined such that two lines are nearly collinear. Thus, a portion of the microarray that is irradiated with the combined radiation line will be irradiated with the nearly collinear lines of radiation. The two lines are typically separated by a distance equivalent to the width of each line in order to minimize crosstalk between channels.

As illustrated diagrammatically in FIG. 14, the microarray 14 may be supported on a stage that allows for proper focusing and movement of the microarray before and during imaging. The stage can be configured to move the sample, thereby changing the relative positions of the rectangular image and the rectangular detector array in the scan-axis (vertical) dimension. Movement of the translation stage can be in one or more dimensions including, for example, one or both of the dimensions that are orthogonal to the direction of propagation for the radiation line and typically denoted as the x and y dimensions. In particular embodiments, the translation stage can be configured to move in the direction perpendicular to the scan axis for a detector array. A stage useful in the invention can be further configured for movement in the dimension along which the radiation line propagates, typically denoted as the Z dimension. Movement in the Z dimension can be useful for focusing the apparatus. In the configuration of FIG. 14, the stage component include tilt actuators 140, typically used for focusing the radiation line, Y-direction actuators and eject components 142 for placing the microarray in a position for scanning, and for gross movements of the microarray between scans, and an X-direction actuators 144 for fine movements of the microarray during scanning.

Sites on the microarray 14 may fluoresce at wavelengths corresponding to those of the excitation beam and return radiation for imaging. As will be appreciated by those skilled in the art, the wavelength at which the dyes of the sample are excited and the wavelength at which they fluoresce will depend upon the absorption and emission spectra of the specific dyes. Such returned radiation will propagate through beam splitter 136 as indicated generally by retrobeam 146 in FIG. 14. This retrobeam will generally be directed toward one or more detectors for imaging purposes. In the illustrated embodiment, for example, the beam is directed toward a mirror 148 and therefrom to a second dichroic beam splitter 150. A portion of the beam, as indicated by reference numeral 154, is then directed by mirrors 152 to a bandpass filter wheel 158 that filters the beam to obtain the desired output wavelength corresponding to one of the fluorescent dyes of the sites in the microarray. In particular embodiments, the portions of the beam that are directed to different mirrors can be the respective lines of a combined beam that forms two nearly co-linear lines. A projection lens 160 then directs the filtered beam to a charge coupled device (CCD) sensor 164 which produces output signals corresponding to locations of the radiation in the received beam. Similarly, a second portion 156 of the beam from beam splitter 150 is directed to another mirror through a different bandpass filter wheel 158 and projection lens 160. The second beam 156 may also be directed through an optional chromatic aberration compensation device 162, which may be motorized. The chromatic aberration compensation device 162 serves to bring both wavelength channels into co-focus. Finally, beam 156, filtered and focused by filter wheel 158 and lens 160 is directed to a second CCD sensor 166. The receipt and processing of signals from the sensors 154 and 166 may be managed by a control board 168.

A rectangular detector array of the invention can be configured to form a virtual slit as set forth previously herein. In particular embodiments, the size and dimensions of the virtual slit can be determined from the ratio of the vertical dimension for the rectangular detector array and the product of the Rayleigh resolution of the imaging optics multiplied by the magnification of the imaging optics. For example, the ratio of the vertical dimension for the rectangular detector array and the product of the Rayleigh resolution of the imaging optics multiplied by the magnification of the imaging optics can be in the range of 0.1 to 10 or in the range of 0.5 to 3. An apparatus of the invention can be configured to obtain an image of a sample at a desired or optimal Rayleigh resolution including, for example, a Rayleigh resolution between 0.2 and 10 micrometers.

In particular embodiments, the aspect ratio of the number of detection elements in a first dimension to the number of detection elements in the scan-axis dimension for a rectangular detector array can be greater than 2, 10, 20, 50, 100, 1000 or higher. For example, a line scan CCD camera can be configured to capture, four thousand (4,000) pixels in the first dimension and n pixels in the scan-axis (vertical) dimension. The CCD line scan camera can be designed such that the resolution along the length of the line is matched to the system resolution. In this case, the horizontal axis includes approximately 4,000 CCD elements along the length of a 2 mm radiation line, resulting in a 0.5 μm pixel resolution at the object. The number of CCD elements "n" in the direction perpendicular to the horizontal axis, also referred to as the vertical axis, can be chosen to collect substantially all of the emitted radiation while reducing the amount of background radiation collected. According to one embodiment of the invention, the CCD has 4096 pixels, each 12 μm in size. To image a 2 mm line to this size CCD requires a magnification of 25×. Accordingly, n can be in the range of six to eight pixels. The design architecture limits the excitation error in the confocal axis such that predominantly 100% of the excitation radiation is contained within a spot comparable with the resolution of the system. In this case, the spot size would be roughly 1.0 μm.

Although the apparatus has been exemplified above with regard to a CCD line scan camera, it will be understood that any of a variety of other detectors can be used including, but not limited to a detector array configured for TDI operation, a CMOS detector, APD detector, Geiger-mode photon counter or other detector set forth elsewhere herein.

In general, the operation of the various components illustrated in FIG. 14 may be coordinated by system controller 170. In a practical application, the system controller will include hardware, firmware and software designed to control operation of the lasers, movement and focusing of the objective 138 and microarray support, and the acquisition and processing of signals from the sensors 164 and 166. The system controller may thus store processed data, and further process the data for generating a reconstructed image of the irradiated sites that fluoresce on the microarray.

Figure 15:
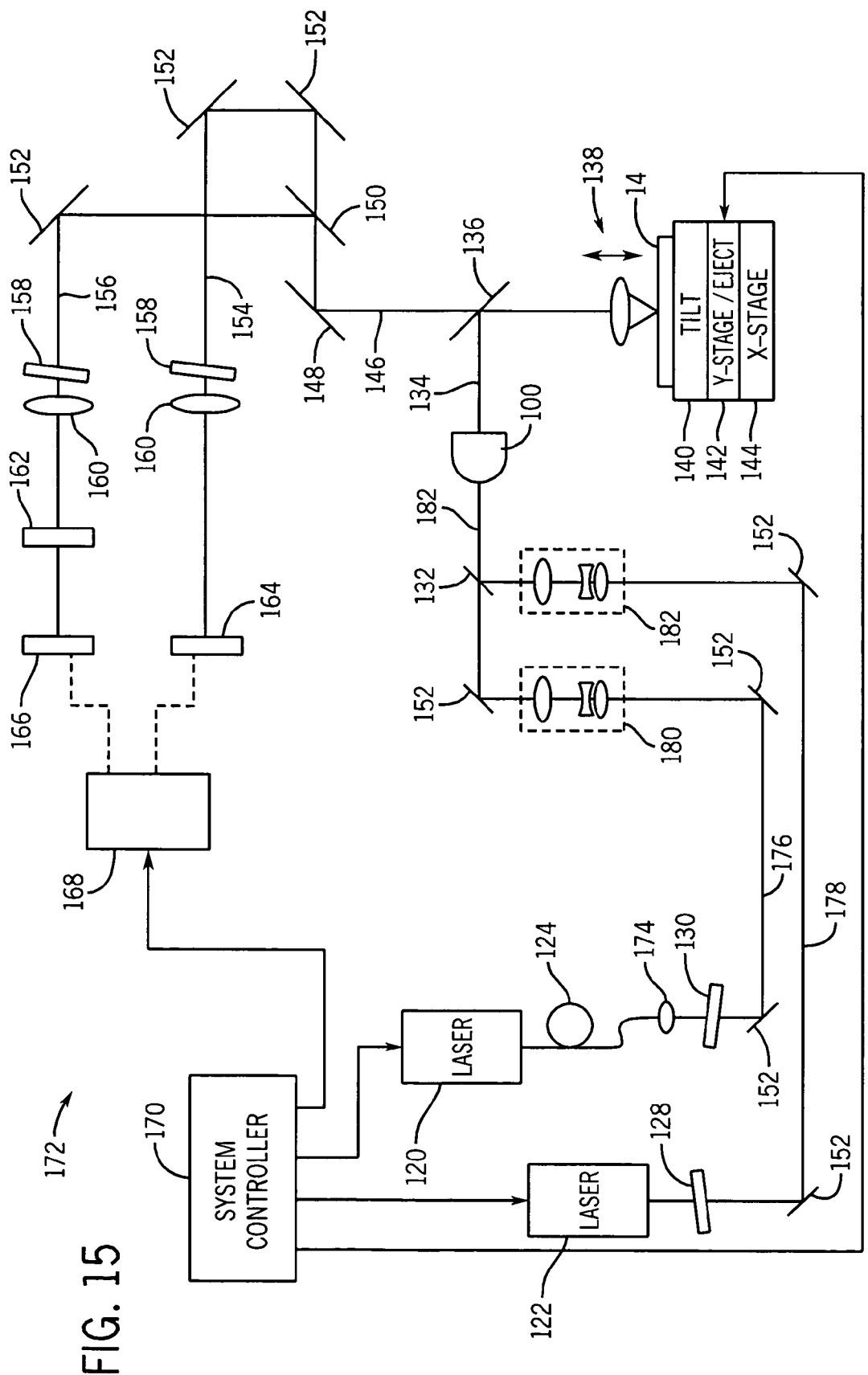
FIG. 15 is a diagrammatical overview of an alternative arrangement for multi-wavelength confocal line scanning of a microarray.

FIG. 15 illustrates an alternative arrangement for the multiple wavelength scanner, designated generally by reference numeral 172. In this alternative arrangement, beams from separate lasers are combined and the cross section of the combined beam then converted to a linear shape by an aspherical lens. Thus, as in the previous embodiment summarized with reference to FIG. 14, input lasers 120 and 122 provide wavelengths of light corresponding to dyes used at various sites on a microarray 14. In the embodiment 172, however, a first laser 120 outputs its beam to a single mode fiber 124, followed by a collimator 174 that collimates this output. The collimated output may then be directed to a filter wheel 130, and the resulting beam 176 is directed, by mirrors 152 to a variable beam expander 180 of the type described above with reference to FIG. 12.

Similarly, output from the second laser 122 is directed through a second filter wheel 130 and the resulting beam 178 is directed, such as via mirrors 152 to a second variable beam expander 182. Output from the variable beam expanders, then, is joined by a beam combiner 132. The combined beam 182, which will include light at the desired wavelengths for radiation of the microarray is converted to a line by an aspherical lens 100. As before, then, a combined radiation line 134 including light at the desired wavelengths will be produced and directed to the microarray 14 by a beam splitter 136. The remaining components of the system may be essentially identical to those described above with respect to FIG. 14.

Figure 16:
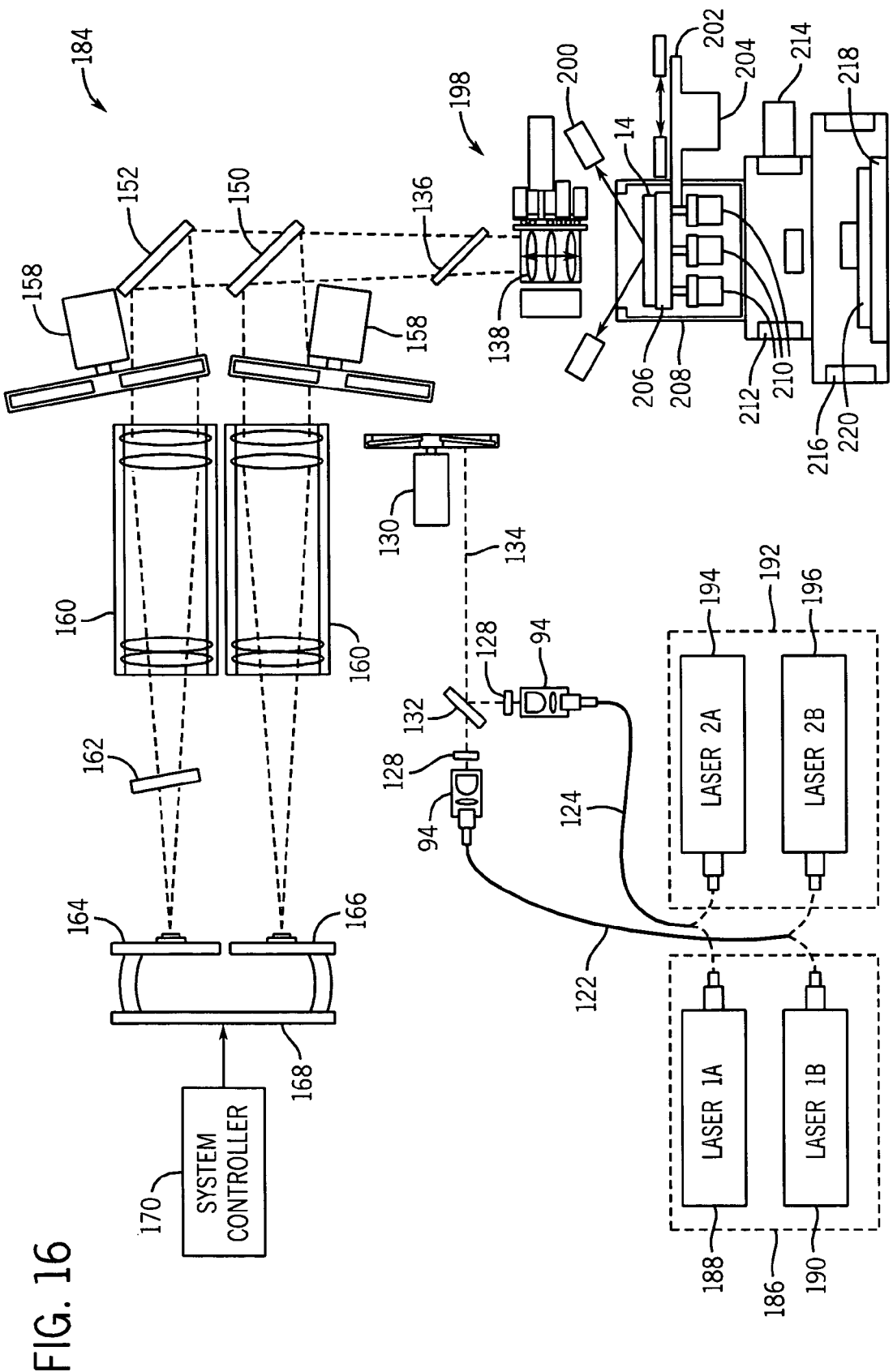
FIG. 16 is an opto-mechanical diagrammatical representation of a presently contemplated implementation for multi-wavelength confocal line scanning of a microarray.

FIG. 16 provides a somewhat more detailed opto-mechanical diagrammatical representation of a multiple wave-length scanner in accordance with aspects of a presently contemplated embodiment. The scanner 184 may include a first laser assembly 186 which, itself, includes multiple lasers. In the illustrated embodiment, for example, laser assembly 186 includes a first laser 188 which may be a 488 nm laser, and a second laser 190 which may be a 658 nm laser. The system may further include a second laser assembly 192, which may include, for example, a 594 nm laser 194 and a 750 nm laser 196. As will be appreciated by those skilled in the art, the inclusion of multiple laser assemblies 190 and 192 may allow for different types of scanning operations to be performed with a single scanner, such as decoding functions, analytical functions, and so forth. For example, lasers 188 and 190 may be used in conjunction with one another for certain types of decoding operations, while lasers 194 and 196 may be used in conjunction with one another for other types of decoding. The assemblies may include other lasers which may alternatively be used, or other assemblies may be provided, such as an assembly employing a 635 nm laser and a 532 nm laser, such as for certain analytical operations.

The laser assemblies 190 and 192 are coupled to single mode fibers 122 and 124 that, as described above, convert the output of the lasers to near pure Gaussian distributions. The light transmitted via the fibers 122 and 124 is input to line generator modules 94 to produce radiation lines. The beams of radiation are then directed to excitation filters 128, and combined by combiner 132 to form a combined radiation line 134. A filter wheel 130 may filter this combined radiation line, such as to block, pass or attenuate the beam as desired.

As in the embodiments described above, the filtered combined radiation line is then directed to a beam splitter 136 and therefrom to an objective 138. In the embodiment illustrated in FIG. 16, the objective is provided with an autofocus system 198 that may include one or more actuators, such as a voice coil, a linear motor stage, a piezo motor stage, or a piezo flexure stage. Sensors 200 provide for sensing the distance or focus of the system on the microarray 14, and serve to provide feedback for dynamic focusing of the confocally-directed radiation line on the appropriate depth along the microarray 14.

FIG. 16 also provides somewhat more detail regarding a presently contemplated arrangement for moving the microarray 14 prior and during scanning. For example, a sample handling tray 202 is provided along with a motor 204 for moving the tray in and out of an imaging position. An adapter plate 206 allows for positioning of the microarray in a docking station 208. Actuators 210 provide for appropriate positioning of the microarray in the docking station. A coarse stage 212, controlled by a stepper motor 214 allows for coarse control of the position of the microarray with respect to the combined radiation line confocally directed toward the microarray. The coarse stage 212 may, for example, be used to appropriately position a portion of the microarray on which the sites are located that are to be imaged. A precision stage 216, which may include a linear motor 218 and a linear encoder 220 serve to provide for fine positioning and movement of the microarray prior to and during scanning.

As before, radiation resulting from fluorescence of individual sites on the microarray is returned through the beam splitter 136 to mirrors or other optical devices used to direct the retrobeam through bandpass filters 158, projection lenses 160 and ultimately to CCD sensors 164 and 166.

Figure 17:
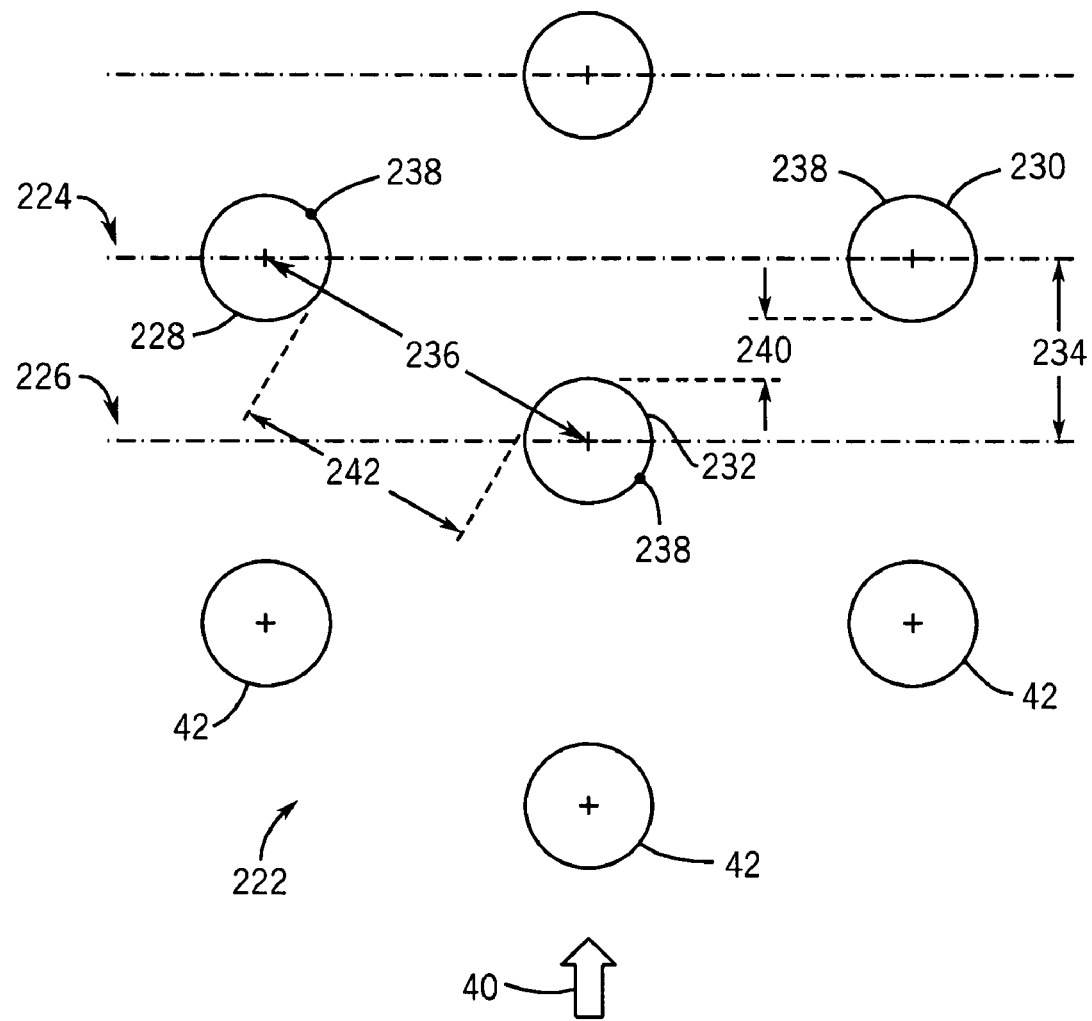
FIG. 17 is a diagrammatical view of a series of individual sites on a biological microarray, illustrating how the confocal line scanning of the present invention improves accuracy by reducing the potential crosstalk, particularly in certain types of layout of the sites on the micorarray with respect to radiation lines used in imaging.
Figure 18:
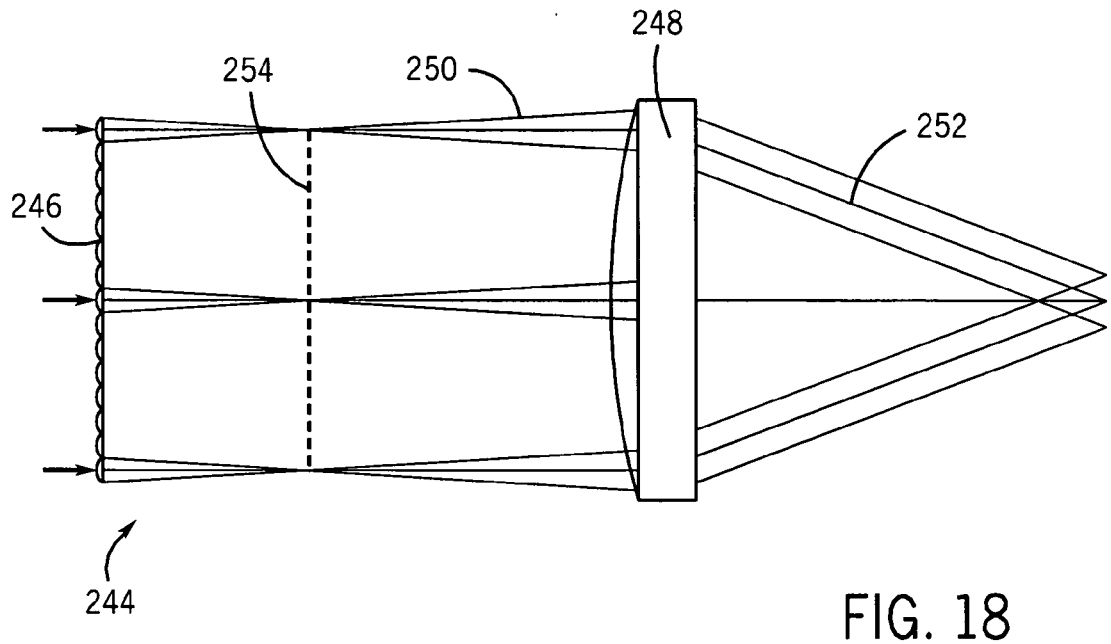
FIGS. 18 through 21 are diagrammatical views of exemplary radiation line generators that may be suitable for use in the invention.

The foregoing arrangements provide for extremely rapid and accurate imaging of multiple sites on a microarray by use of a radiation line that excites the sites simultaneously. It has been found that the confocal line scanning technique of the present invention is particularly useful in applications where sites on the microarray are spaced from one another such as to, in combination with the linear scanning described above, reduce the potential for crosstalk between returned radiation from the individual sites. FIG. 17 illustrates a presently contemplated arrangement of sites in a hexagonal grid array to take advantage of this aspect of the confocal line scanning technique of the invention.

As illustrated in FIG. 17, an array section 222 will include a plurality of sites 42 provided in a predetermined pattern. A presently contemplated embodiment provides a hexagonal packing pattern as illustrated. The pattern includes what may be termed adjacent rows or lines of sites designated by reference numerals 224 and 226 in FIG. 17. As will be appreciated by those skilled in the art, the orientation of the lines may generally be thought of with reference to the direction of scanning by the confocally directed radiation line described above. As radiation is directed along lines parallel to the site lines 224 and 226, then, a portion of the lines of sites will be illuminated by the radiation, and return a retrobeam which will be bright in those areas that fluoresce. Adjacent sites 228 and 230 in each row or line of sites will be spaced from one another, and both of these sites will be spaced from a nearest adjacent site, such as site 232 of an adjacent row or line 226. The distance between successive or adjacent lines of sites may be designated generally by reference numeral 234, such as by reference to the center of the sites in each line. It will be noted that with the hexagonal packing pattern of FIG. 17, the distance between the centers of adjacent sites in the same line, however, is greater than the distance between the adjacent lines of sites. Moreover, in the orientation of FIG. 17, the distance between centers of adjacent sites in the same line is greater than the nearest distance 236 between sites in the adjacent lines. In particular, for a hexagonal packing pattern of the type illustrated in FIG. 17, distance 234 will be approximately 0.866 (the cosine of 60 degrees) of the distance 236.

Moreover, if the sites 228, 230 and 232 are considered to have edges 238, these edges will be spaced from one another by a distance greater than would result if the sites were disposed in a rectilinear pattern. That is, the projection of the distance between the edges 238 of sites 228 and 232 along the axis of scanning may be denoted by reference numeral 240. The actual distance, however, between the edges will be greater, as indicated by reference numeral 242. Again, for the hexagonal pattern illustrated in FIG. 17, the distance 242 will be approximately 15% greater than the distance 240.

As will be appreciated by those skilled in the art, as the density of the sites on microarrays is increased, and spacing between the sites is consequently decreased, increasing demands are made on the ability to carefully focus the irradiating light beam on the sites, and to properly focus the retrobeam for imaging purposes. The present technique provides excellent results in the ability to confocally irradiate a line of sites, where the confocality exists in the axis parallel to the width of the radiation line and not along the length of the radiation line. However, crosstalk between the sites may be considered as a relative inability to distinguish between the sites, as the images produced from high intensity sites spills over in the nonconfocal axis to neighboring sites. This can be, problematic, for example, when high intensity sites are located immediately adjacent to very low intensity sites. The combination of confocal line scanning with non-rectilinearly packed sites, in particularly in combination with hexagonally packed sites is believed to provide far superior distinction between irradiated and imaged sites, due to the reduction in crosstalk and blurring between the imaged sites.

The combination of a hexagonal arrangement of sites and the radiation line orientation set forth above is one example of an embodiment of the invention wherein the distances between nearest neighbor sites that are irradiated simultaneously by a radiation line at a first scan position is greater than the distance between nearest neighbor sites that are irradiated at different times by the scanning radiation line. It will be understood that other combinations of site packing and line orientation can also be used to achieve similar advantages. For example, although circular sites in a rectilinear grid are not packed as closely as in a hexagonal grid, the orientation for a radiation line and its direction of scan can be selected for a desired reduction in cross-talk. More specifically, the radiation line can be oriented diagonally with respect to the rows and columns of sites in the rectilinear grid and the radiation line can be scanned across the grid in the diagonal direction to achieve less cross talk between the sites than if the radiation line was oriented orthogonally with respect to the rows and columns of sites in the rectilinear grid and scanned in the orthogonal direction. An advantage being that the line is oriented such that the greatest spacing between adjacent sites occurs in the nonconfocal axis, parallel to the radiation line.

The packing arrangements described above are particularly useful when used with a radiation line that is substantially narrower than the width of the sites being irradiated. In particular embodiments, the width of the radiation line (i.e. the shorter dimension of the line) will be at most 75%, 66%, 50%, 30%, 25% or 10% of the width of the sites being irradiated. Generally, sites having a regular shape are preferred, for example, sites having reflectional symmetry or rotational symmetry. However, irregular shaped sites can be used if desired for a particular application. Whether a site is regular or irregular in shape the width for the site will typically be measured at the widest dimension, for example, width is measured as the diameter of a site having a circular cross-section.

As illustrated in FIGS. 18-23, a diffraction-limited line with uniform intensity distribution can be generated using a number of architectures. In one such embodiment, shown in FIG. 18, the line generator 244 can be formed with a cylindrical micro-lens array 246 and a condenser 248. A cylindrical micro-lens array 246 is used to focus the excitation beam 250 to the front focal plane of a condenser 248 in one dimension while leaving a second dimension unaffected. A diffraction-limited line 252 with uniform intensity distribution will be generated on the back focal plane of the condenser 248. The uniformity of the line is related to the number of cylindrical micro-lenses 246 that cover the entrance pupil of the condenser 248. The greater the number of cylindrical micro-lens arrays 246, the more uniform the line intensity distribution will be.

Figure 19:
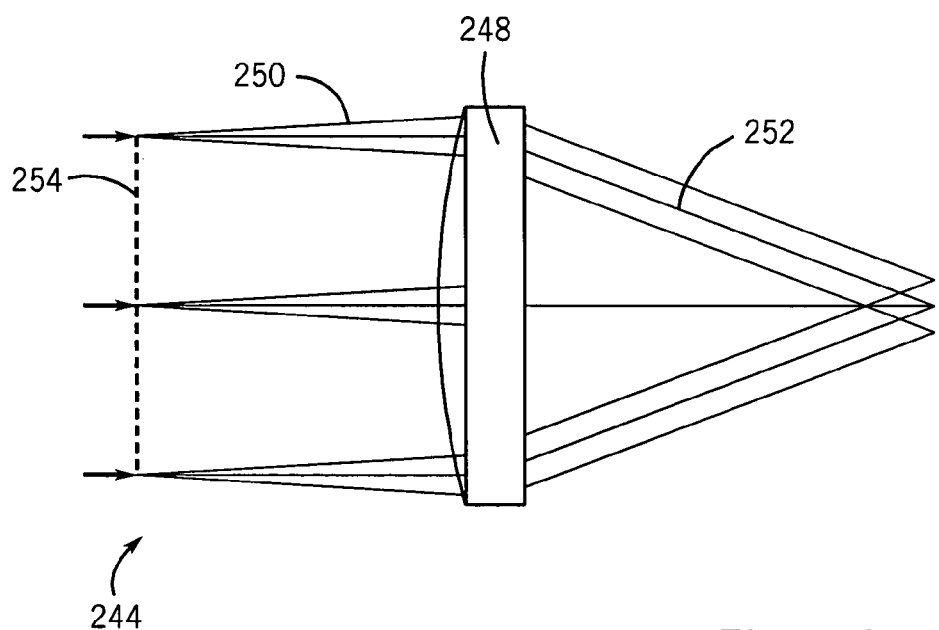

According to another embodiment and as shown in FIG. 19, the line generator 244 can be formed with a one-dimensional diffuser 254 and a condenser 248. A one-dimensional diffuser 254 having an angular uniformity is placed at the front focal plane of a condenser 248. The diffuser 254 fans the input collimated beam 250 in one dimension and leaves another dimension unaffected. A diffraction-limited line 252 with uniform intensity distribution will be generated on the back focal plane of the condenser 248. Since the diffuser 254 has angular uniformity, the generated line will be uniform.

In still another embodiment of the invention, an objective 256 is used as a condenser 248. Preferably, the objective lens 256 is a telecentric lens with an external pupil size of 15.75 mm. Preferably, this size is configured to match the diameter of the collimated input excitation beam 250. In addition, the input field angle of the lens is +/−3 degrees, which corresponds to a field view of 2 mm.

Figure 20:
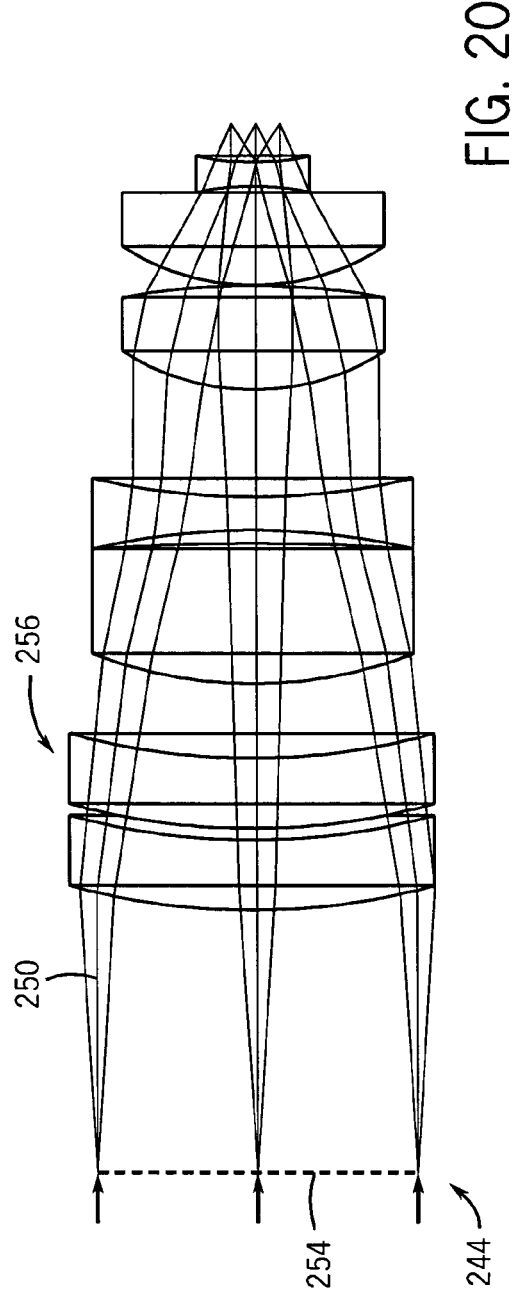

FIG. 20 shows a one-dimensional diffuser 254 in use with the objective 256 described above. As shown in FIG. 20, a one-dimensional diffuser 254 is placed at the pupil stop of the objective 256. The objective 256 diffuses the collimated input beam 250 to different angles in a certain range in one dimension and leaves another dimension unaffected. The diffuser 254 has angular uniformity, i.e. the intensities of beams diffused to different angles are the same. The lens 256 focuses the beam at each particular angle to a point in the line. The uniformity of the line is determined by the angular sensitivity of the diffuser 254. In addition, the length of radiation line 268 is determined by the fan angle of the diffuser 254. The larger the fan angle is, the longer the generated radiation line 268 will be. If the fan angle of the diffuser 254 is +/−3°, the generated line length will be 2 mm. Although the length of the radiation line 268 can be longer than 2 mm, a desired uniformity can be obtained by a line 2 mm in length.

Figure 21:
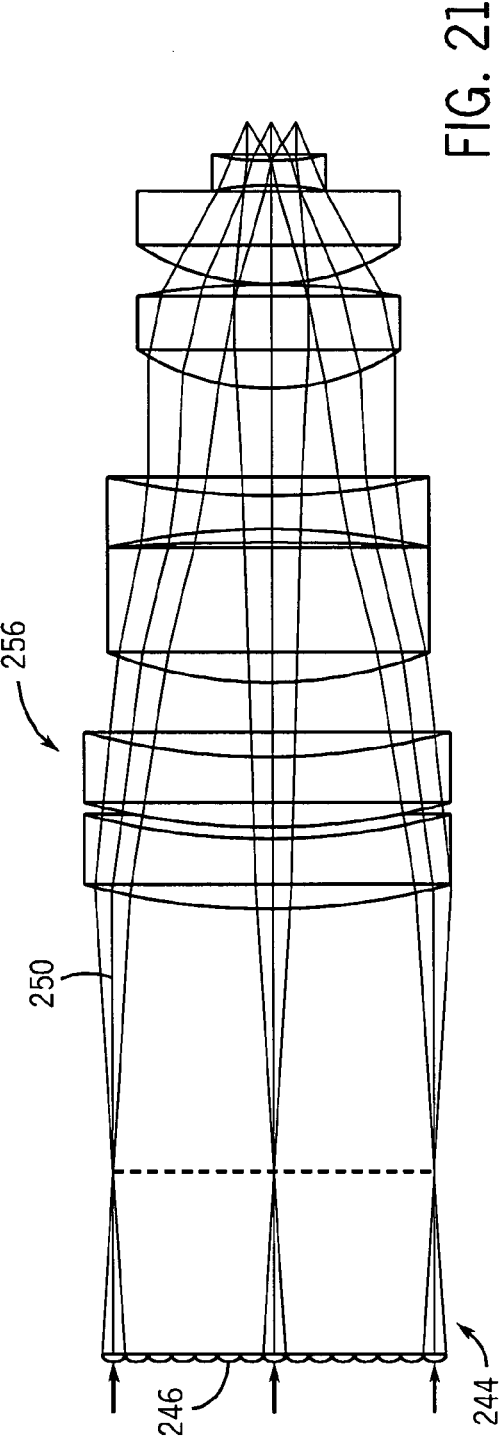

According to another embodiment, FIG. 21 shows a cylindrical micro-lens array 246 in use with the above-described objective 256. Each cylindrical micro-lens 246 samples a portion of the collimated input beam 250, focuses it to the pupil stop of the objective 256 in one dimension, and leaves the second dimension unaffected. The cylindrical micro-lens array 246 fans the beam 250 to different angles in a certain range in one dimension. The fan angle is determined by the f-number of the cylindrical micro-lenses 246. The objective lens 256 focuses the beam 250 at each angle to a point in the line. Since each point in the focused line gets contribution from all the cylindrical micro-lenses 246, the uniformity of the line is related to the number of cylindrical micro-lenses 246 that covers the entrance pupil of the objective lens 256. For example, according to one embodiment of the invention, 158 micro-lenses are used to cover the pupil stop in order to generate a uniform line excitation 268.

Figure 22:
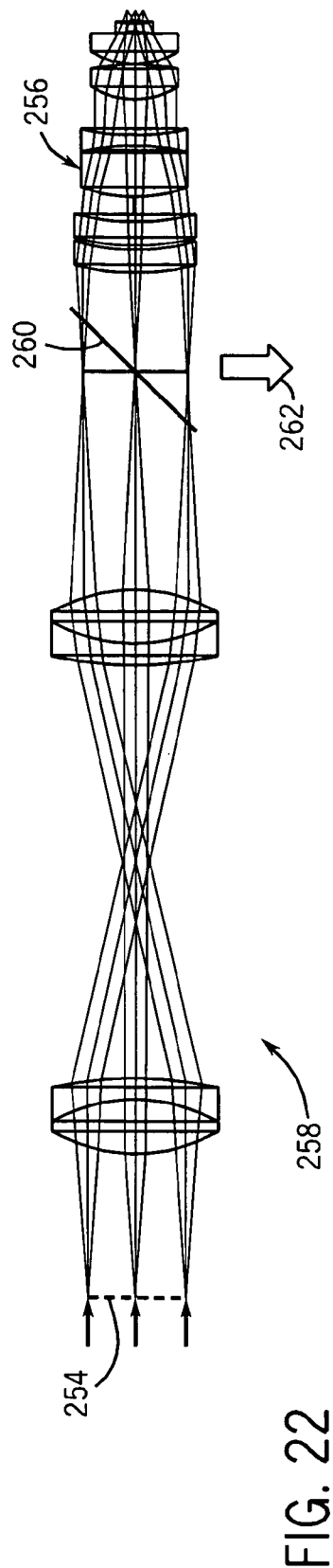
FIGS. 22 and 23 are diagrammatical views of line generators in a fluorescence imaging system, suitable for use in the invention.
Figure 23:
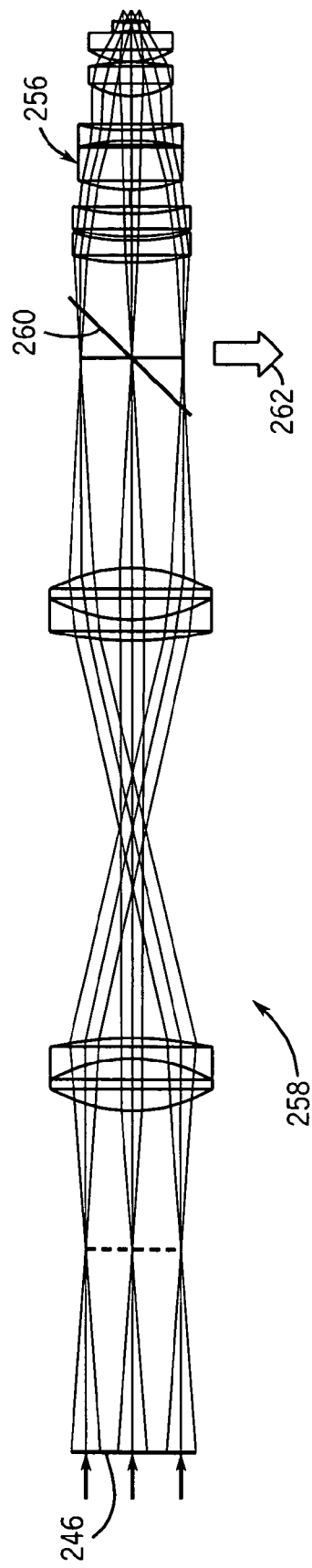

FIGS. 22 and 23 show additional embodiments of relay telescopes, configured for fluorescent imaging. A relay telescope 258 is positioned between the one-dimensional diffuser 254 (see FIG. 22) or cylindrical micro-lens array 246 (see FIG. 23) and a dichroic beam splitter 260. The dichroic beam splitter 260 is configured to separate the fluorescence imaging path (retro-beam) 262 from the excitation path 250.

A CCD camera or other detector array used in the invention can be configured for binning. Binning increases the detector array's sensitivity by summing the charges from multiple pixels in the array into one pixel. Exemplary types of binning that can be used include horizontal binning, vertical binning, or full binning. With horizontal binning, pairs of adjacent pixels in each line of a detector array are summed. With vertical binning, pairs of adjacent pixels from two lines in the array are summed. Full binning is a combination of horizontal and vertical binning in which four adjacent pixels are summed.

Binning in the invention can be carried out with larger sets of sensor elements. As illustrated in FIG. 24(a), the line scan CCD camera and corresponding control electronics can be configured such that all pixel elements in the vertical axis are collected in a common bin and read out as a single value. Thus, binning need not be limited to adjacent pairs or adjacent groups of array elements. Accordingly, a set of more than 2 sensor elements, such as pixels of a CCD camera, can be binned even if the set includes non-adjacent sensor elements. Non-adjacent sensor elements occur, for example, in a linear arrangement of 3 sensor elements where the first and third elements are separated from each other by the intervening second sensor element.

As shown in FIG. 24(b), in binning, all of the pixels in a row are shifted out at once after a single integration time. The advantage of this approach, when used in an apparatus of the invention, is that compared to a common TDI design the readout rate is less sensitive to jitter. Furthermore, the apparatus would have confocality in one axis, and the tolerance of the synchronization timing of the readout with the Y-stage movement would be reduced. FIG. 24(b) shows the projection of a 1 μm laser spot on a line scan CCD camera. The projection is symmetrical in both the X and Y-axis. Limiting the number of CCD pixels to 6 in the vertical axis creates a virtual slit in that axis. The same effect can be achieved with a TDI camera, the main requirement is that the number of pixels in the vertical axis be optimized to pass a signal while also rejecting background noise. To achieve this, the laser spot size is set to match the resolution of the system in conjunction with limiting the number of vertical pixels.

An alternate embodiment of the invention uses a TDI design which limits the number of vertical pixels such that the virtual slit is still created. As shown in FIG. 24(c), in TDI, pixels are shifted in sync with the encoder output of the y-stage. Additionally, the advantage over system designs where n=1 are that the collection efficiency of the system would be increased and the sensitivity to small optical alignment drifts would be decreased. Exemplary TDI designs and methods that can be used in the invention are described in U.S. Pat. No. 5,754,291, which is incorporated herein by reference.

According to another embodiment of the invention, the present scanning system architecture is configured to use parallel multi-spectral fluorescence imaging using line-scan imaging sensors. As shown in FIG. 25, radiation line 134 is used to excite fluorescent molecules in a full spectral range and a chromatic dispersion element 264 is used to spread the line fluorescence image 262 across multiple line-scan imaging sensors 266. The system can be implemented using side illumination or collinear illumination. According to this embodiment of the invention, a multi-band filter set 268 is used to excite and detect multiple fluorescent molecules. As represented in FIG. 26, each of the plurality of sensors 266 is mapped to a narrow band spectral range. The sensors 266 can be imaging sensors such as a linear line-scan CCD or a TDI line-scan CCD. Sensors are also referred to as detectors herein.

As shown in FIG. 27, according to still another embodiment of the invention, the scanning system architecture can be configured to use a multi-line illumination technique. The system can be implemented using side illumination or collinear illumination. Here, each line 268 excites a sample region at a different wavelength, for example, to excite different fluorescent molecules. The resulting multi-line fluorescence image is collected by a detector 266 with multiple line-scan imaging sensors 266. Each sensor 266 generates the corresponded fluorescent image. Because the fluorescence with different spectral ranges is already spatially separated, no chromatic dispersion element 264 is required. A multi-notch filter 270 is used to effectively block residual Rayleigh and Raman scattered radiation.

Further, if a chromatic dispersion element is used in the system of FIG. 27, images with higher spectral resolution can be collected. As illustrated in FIG. 28, each sensor group 266 in the figure can also work in TDI mode to generate a single integrated image, which provides images with hierarchical spectral resolution.

The scanning system architecture can be designed to excite fluorescence of multiple dyes in different spectral ranges simultaneously. Exemplary architectures include a single line with multi-colors used in the system of FIG. 25 or spaced multi-lines with multi-colors used in the system of FIG. 27. The radiation source can be a white light lamp with a multi-band excitation filter or a combination of multiple lasers. The excitation filter of the multi-band filter set 268 in the system of FIG. 25 is not required, for example, if the combination of multiple lasers is used as the radiation source. In addition, the illumination can be collinear illumination (illumination shares the same objective lens 138 as the collection) as shown in FIG. 24 or slide illumination (dark field) as shown in FIG. 28. A multi-band dichroic beam splitter 136 (shown in FIG. 25) can be used for the collinear illumination and omitted for the side illumination embodiment. Also as shown in FIG. 25, a multi-band emission filter 272 of the multi band filter set 82 can be used to selectively block excitation radiation while passing fluorescence bands. For illumination with multiple lasers, a multi-notch filter 270 can also be used to selectively block excitation radiation while passing fluorescence bands, which provides even more efficient florescence detection.

According to particular embodiments of the invention, emission filters 272 can be integrated with the image sensor 266. An exemplary orientation is shown in FIG. 29. A different orientation for blocking multi-band illumination and multiple laser illumination is shown in FIGS. 30(a) and 30(b) respectively.

An apparatus or method of the invention is particularly useful for obtaining an image of a 2-dimensional area of a sample. Thus, if desired, detection can be substantially restricted to obtaining an image in 2 of the 3 possible dimensions for a sample. Accordingly, an image of a surface for a sample of interest can be detected or imaged. A particularly relevant sample is a microarray. Using the invention the surface of a microarray can be detected or imaged to determine one or more property of the microarray. Exemplary properties of a microarray that can be detected include, but are not limited to, the presence or absence of a label, the location of a label at a particular location such as a location where a particular probe resides, or a specific characteristic of a label such as emission of radiation at a particular wavelength or wavelength range.

Detection of such properties for a microarray can be used to determine the presence or absence of a particular target molecule in a sample contacted with the microarray. This can be determined, for example, based on binding of a labeled target analyte to a particular probe of the microarray or due to a target-dependent modification of a particular probe to incorporate, remove or alter a label at the probe location. Any one of several assays can be used to identify or characterize targets using a microarray as described, for example, in U.S. Pat. App. Pub. Nos. 2003/0108867, 2003/0108900, 2003/0170684, 2003/0207295, or 2005/0181394, each of which is hereby incorporated by reference.

Exemplary labels that can be detected in accordance with the invention, for example, when present on a microarray include, but are not limited to, a chromophore; luminophore; fluorophore; optically encoded nanoparticles; particles encoded with a diffraction-grating; electrochemiluminescent label such as Ru(bpy)268+; or moiety that can be detected based on an optical characteristic. Fluorophores that are useful in the invention include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066, each of which is hereby incorporated by reference.

Any of a variety of microarrays known in the art, including, for example, those set forth elsewhere herein, can used as a sample in the invention. A typical microarray contains sites, sometimes referred to as features, each having a population of probes. The population of probes at each site typically is homogenous, having a single species of probe but in some embodiments the populations can each be heterogeneous.

Sites or features of an array are typically discrete, being separated with spaces between each other. The size of the probe sites and/or spacing between the sites can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful in the invention can have sites that are separated by less than 100 μm, 50 μm, 10 μm, 5 μm, 1 μm or 0.5 μm. An apparatus or method of the invention can be used to image an array at a resolution sufficient to distinguish sites at the above densities or density ranges.

Although the invention has been exemplified above with regard to the use of a microarray as a sample, it will be understood that other samples having features or sites at the above densities can be imaged at the resolutions set forth above. Other exemplary samples include, but are not limited to, biological specimens such as cells or tissues, electronic chips such as those used in computer processors, or the like. A microarray or other sample can be placed in a sample region of an apparatus of the invention by being placed on a sample stage such as those described elsewhere herein.

An apparatus of the invention can further include a processor, operably coupled to a rectangular detector array or otherwise configured to obtain data from the rectangular detector array, wherein the processor is configured to perform a plurality of functions on the image. The processor can include a conventional or general purpose computer system that is programmed with, or otherwise has access to, one or more program modules involved in the analysis of imaging data. Exemplary computer systems that are useful in the invention include, but are not limited to personal computer systems, such as those based on Intel®, IBM®, or Motorola® microprocessors; or work stations such as a SPARC® workstation or UNIX® workstation. Useful systems include those using the Microsoft® Windows®, UNIX or LINUX® operating system. The systems and methods described herein can also be implemented to run on client-server systems or wide-area networks such as the Internet.

The processor can be included in a computer system, configured to operate as either a client or server. The processor can execute instructions included in one or more program modules. Results from one or more program modules such as an image of a sample or sample region, or analysis of the sample or sample region can be reported to a user via a graphical user interface. For example, results can be reported via a monitor or printing device operably connected to the processor. Thus, an image of an array or other sample can be provided to a user via a graphical user interface.

According to certain aspects of the invention, several advantages are realized. The system of the present invention scans samples faster than other technologies and provides improved data quality at lower cost. Specifically, the readout rate of the present invention is increased by a factor of n as compared to conventional TDI systems. Confocality can be achieved in one or more axis. In addition, the present invention is less sensitive to optical alignment drifts.

Further, the present invention combines the advantages of simultaneous excitation/detection of multiple fluorescent molecules using multi-band filters and parallel readout of multiple line-scan imaging sensors on the same sample. The present invention can simultaneously generate multi-spectral fluorescence images in a fast speed. In particular embodiments, an apparatus of method of the invention can scan a sample at a rate of at least about 0.01 mm$^2$/sec. Depending upon the particular application of the invention faster scan rates can also be used including, for example, in terms of the area scanned, a rate of at least about 0.02 mm$^2$/sec, 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec or 100 mm$^2$/sec or faster. If desired, for example, to reduce noise, scan rate can have an upper limit of about 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec or 100 mm$^2$/sec. Scan rate can also be measured in terms of the rate of relative movement for an image and detector in the scan-axis (vertical) dimension and can be, for example, at least about 0.1 mm/sec, 0.5 mm/sec, 1 mm/sec, 10 mm/sec, or 100 mm/sec. Again, to reduce noise, scan rate can have an upper limit of about 0.5 mm/sec, 1 mm/sec, 10 mm/sec, or 100 mm/sec. In sum, the present invention can be used to build multi-spectral fluorescence imagers, which are more efficient and cost-effective than other imaging systems.

The following are terms that are used in the present discussion, and which are intended to have the meanings ascribed below.

As used herein, the term "radiation source" is intended to mean an origin or generator of propagated electromagnetic energy. The term can include an illumination source producing electromagnetic radiation in the ultra violet (UV) range (about 200 to 390 nm), visible (VIS) range (about 390 to 770 nm), or infrared (IR) range (about 0.77 to 25 microns), or other range of the electromagnetic spectrum. A radiation source can include, for example, a lamp such as an arc lamp or quartz halogen lamp, or a laser such as a solid state laser or a gas laser or an LED such as an LED/single mode fiber system.

As used herein, the term "excitation radiation" is intended to mean electromagnetic energy propagated toward a sample or sample region. Excitation radiation can be in a form to induce any of a variety of responses from a sample including, but not limited to, absorption of energy, reflection, fluorescence emission or luminescence.

As used herein, the term "sample region" is intended to mean a location that is to be detected. The location can be, for example, in, on or proximal to a support device that is configured to support or contain an object to be detected. A sample can occupy a sample region permanently or temporarily such that the sample can be removed from the sample region.: For example a sample region can be a location on or near a translation stage, the location being occupied by a microarray when placed on the translation stage.

As used herein, the term "detector array" is intended to mean a device or apparatus having several elements that convert the energy of contacted photons into an electrical response. An exemplary detector array is a charge coupled device (CCD), wherein the elements are photosensitive charge collection sites that accumulate charge in response to impinging photons. Further examples of detector arrays include, without limitation, a complementary metal oxide semiconductor (CMOS) detector array, avalanche photodiode (APD) detector array, or a Geiger-mode photon counter detector array. The elements of a detector array can have any of a variety of arrangements. For example, a rectangular detector array has elements in a 2-dimensional, orthogonal arrangement in which a first dimension, referred to as the "horizontal" dimension is longer than a second dimension referred to as the "vertical" dimension. A square detector array has elements in a 2-dimensional, orthogonal arrangement in which the first and second dimensions of the arrangement are the same length.

As used herein, the term "rectangular image" is intended to mean an optically formed representation of a sample, or portion of the sample, that occurs within a 2-dimensional, orthogonal region having a horizontal dimension that is longer than the vertical dimension. The rectangular image can represent the entirety of an image emanating from a sample region or, alternatively, can be a rectangular portion of a larger image, the larger image having any of a variety of shapes.

As used herein, the term "scanning device" is intended to mean a device capable of sequentially detecting different portions of a sample. A scanning device can operate, by changing the position of one or more component of a detection apparatus including, for example, a sample, radiation source, optical device that directs excitation radiation to a sample, optical device that directs radiation emanating from a sample, or detector array. Exemplary scanning devices include, but are not limited to a galvanometer configured to move a beam or line of radiation across a sample or a translation stage configured to move a sample across a beam or line of radiation.

As used herein, the term "Rayleigh resolution" is RR in the following equation $$RR=((1.22)(\lambda)(f))/D$$

wherein $\lambda$ is wavelength, f is focal length and D is distance between two objects that are detected. The term is intended to be consistent with its use in the art of optics, for example, as set forth in Hecht, *Optics,* 4th ed., Addison Wesley, Boston Mass. (2001), which is hereby incorporated by reference.

As used herein, the term "magnification" is intended to mean the ratio of the size of an object to the size of an image of the object. For example, magnification can be determined from the ratio of the size of sample region (i.e. the object) to the size of an image of the sample region at a detector array. In systems including an objective and projection lens, magnification can be determined from the ratio of focal length of the objective to back focal length of the projection lens.

As used herein, the term "radiation line" is intended to mean a collection of electromagnetic waves or particles propagated in a uniform direction, wherein the 2-dimensional cross section orthogonal to the direction of propagation is rectangular or oblong. Exemplary 2-dimensional cross sections of a radiation line include, but are not limited to, a rectangular, elliptical, or oval shape. The cross sectional width of a radiation line can have one or both dimensions in a range of, for example, about 0.05 μm to about 10 μm. For example, a dimension of the radiation line can be at least about 0.05 μm, 0.1 μm, 0.5 μm, 1 μm, 5 μm or 10 μm. Furthermore, a dimension of a radiation line can be, for example, at most about 0.1 μm, 0.5 μm, 1 μm, 5 μm or 10 μm. It will be understood that these dimensions are merely exemplary and radiation lines having other dimensions can be used if desired.

As used herein, the term "line generator" is intended to mean an optical element that is configured to generate a diffraction-limited or near diffraction-limited radiation line in the plane perpendicular to the optical axis of propagation with a substantially uniform intensity distribution along the horizontal axis of the line. Exemplary line generators include, but are not limited to, a one dimensional diffuser having angular uniformity, cylindrical microlens array, diffractive element or aspheric refractive lens such as a Powell lens. The one dimensional diffuser having angular uniformity or cylindrical microlens array can be placed to direct radiation to a condenser.

As used herein, the term "beam splitter" is intended to mean an optical element that passes a first portion of a radiation beam and reflects a second portion of the beam. For example a beam splitter can be configured to selectively pass radiation in a first wavelength range and reflect radiation in a second, different radiation range. When used for fluorescence detection the beam splitter will typically reflect the shorter wavelength excitation radiation and transmit the longer wavelength emission radiation.

As used herein, the term "external pupil" is used in reference to an objective, where the entrance pupil to the back aperture of the objective is behind the physical dimensions of the objective in the excitation beam path.

As used herein, the term "expander" is intended to mean one or more optical elements configured to adjust the diameter and collimation of a radiation beam. For example, an expander can be configured to increase the diameter of a radiation beam by a desired amount such as at least 2 fold, 5 fold, 10 fold or more. Optical elements of an expander can include, for example, one or more mirrors or lenses.

As used herein, the term "projection lens" is intended to mean an optical element configured to transfer the image of an object to a detector. For example, a lens can be placed to transfer an image emanating from an objective lens to a detector array.

As used herein, the term "optical filter" is intended to mean a device for selectively passing or rejecting passage of radiation in a wavelength, polarization or frequency dependent manner. The term can include an interference filter in which multiple layers of dielectric materials pass or reflect radiation according to constructive or destructive interference between reflections from the various layers. Interference filters are also referred to in the art as dichroic filters, or dielectric filters. The term can include an absorptive filter which prevents passage of radiation having a selective wavelength or wavelength range by absorption. Absorptive filters include, for example, colored glass or liquid.

A filter used in the invention can have one or more particular filter transmission characteristics including, for example, bandpass, short pass and long pass. A band pass filter selectively passes radiation in a wavelength range defined by a center wavelength of maximum radiation transmission (Tmax) and a bandwidth and blocks passage of radiation outside of this range. Tmax defines the percentage of radiation transmitted at the center wavelength. The bandwidth is typically described as the full width at half maximum (FWHM) which is the range of wavelengths passed by the filter at a transmission value that is half of Tmax. A band pass filter useful in the invention can have a FWHM of 10 nanometers (nm), 20 nm, 30 nm, 40 nm or 50 nm. A long pass filter selectively passes higher wavelength radiation as defined by a Tmax and a cut on wavelength. The cut on wavelength is the wavelength at which radiation transmission is half of Tmax; as wavelength increases above the cut on wavelength, transmission percentage increases and as wavelength decreases below the cut on wavelength transmission percentage decreases. A short pass filter selectively passes lower wavelength radiation as defined by a Tmax and a cut off wavelength. The cut off wavelength is the wavelength at which radiation transmission is half of Tmax; as wavelength increases above the cut off wavelength, transmission percentage decreases and as wavelength decreases below the cut off wavelength transmission percentage increases. A filter of the invention can have a Tmax of 50-100%, 60-90% or 70-80%.

As used herein, the term "microarray" refers to a population of different probe molecules that are attached to one or more substrates such that the different probe molecules can be differentiated from each other according to relative location. An array can include different probe molecules, or populations of the probe molecules, that are each located at a different addressable location on a substrate. Alternatively, a microarray can include separate substrates each bearing a different probe molecule, or population of the probe molecules, that can be identified according to the locations of the substrates on a surface to which the substrates are attached or according to the locations of the substrates in a liquid. Exemplary arrays in which separate substrates are located on a surface include, without limitation, a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441, and 6,859,570; and PCT Publication No. WO 00/63437, each of which is hereby incorporated by reference. Other arrays having particles on a surface include those set forth in US 2005/0227252; WO 05/033681; and WO 04/024328.

Further examples of commercially available microarrays that can be used in the invention include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies. Other microarrays that can be used in the invention include, without limitation, those described in Butte, *Nature Reviews Drug Discov.* 1:951-60 (2002) or U.S. Pat Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; and WO 93/17126; WO 95/35505, each of which is hereby incorporated by reference.

As used herein, the term "time delay integration" or "TDI" is intended to mean sequential detection of different portions of a sample by different subsets of elements of a detector array, wherein transfer of charge between the subsets of elements proceeds at a rate synchronized with and in the same direction as the apparent motion of the sample being imaged. For example, TDI can be carried out by scanning a sample such that a frame transfer device produces a continuous video image of the sample by means of a stack of linear arrays aligned with and synchronized to the apparent movement of the sample, whereby as the image moves from one line to the next, the stored charge moves along with it. Accumulation of charge can integrate during the entire time required for the row of charge to move from one end of the detector to the serial register (or to the storage area of the device, in the case of a frame transfer CCD).

As used herein, the term "collection arm" is intended to mean an optical component or set of optical components positioned to direct radiation from a sample region to a detector.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for imaging a microarray comprising:
   a laser light source;
   a single mode fiber optic cable coupled to the laser light source for transmitting laser light in single mode transmission;
   a line illuminator for converting laser light from the source to a line of radiation, the line illuminator including a collimator arranged to receive the laser light from the source and an aspherical lens for converting collimated light from the collimator to the line of radiation; and
   a focusing device for simultaneously directing the line of radiation onto sites of a microarray in one dimension of a two-dimensional plane at the surface of the microarray.

2. The system of claim 1, wherein the line illuminator is configured to convert laser light from the source to a line of radiation of substantially uniform intensity over a desired line length.

3. The system of claim 1, wherein the collimator and aspherical lens are prealigned within a module to permit installation of the module in the system without further alignment within the module during installation.

4. The system of claim 1, wherein the focusing device is configured to create a uniform line of radiation that is diffraction limited in the narrow dimension of the line.

5. The system of claim 3, further comprising a laser line filter disposed in the module intermediate the collimator and the aspherical lens.

6. The system of claim 1, wherein the aspherical lens is a Powell lens.

7. The system of claim 1, wherein the aspherical lens is a cylindrical lens.

8. The system of claim 1, wherein individual sites on the microarray are separated by a distance in the range of about 0.1 to 50 micrometers.

9. The system of claim 8, wherein the system is configured to distinguish the individual sites.

10. The system of claim 1, wherein the system is configured to obtain an image of the microarray at a Rayleigh resolution between about 0.2 and 10 micrometers.

11. The system of claim 1, wherein the line illuminator includes an integral connector, and the single mode fiber optic cable is terminated with a mating connector for coupling to the line illuminator.

12. The system of claim 1, wherein one end of the single mode fiber optic cable is integrally coupled to the line illuminator.

13. The system of claim 1, wherein one end of the single mode fiber optic cable is removably coupled to the line illuminator.

14. The system of claim 1, comprising a second fiber optic cable coupled to the laser light source at one end thereof and coupled to the single mode fiber optic cable at an opposite end thereof.

15. The system of claim 14, wherein the second fiber optic cable is a single mode fiber optic cable.

16. The system of claim 15, wherein the fiber optic cables are coupled to one another via an optical connector.

17. The system of claim 15, wherein the fiber optic cables are spliced to one another.

18. The system of claim 1, wherein the single mode fiber optic cable is configured for single mode transmission of laser light with a wavelength of approximately 405 nm, 488 nm, 532 nm or 633 nm.

19. A system for imaging a microarray comprising:
   a laser light source;
   a fiber optic cable coupled to the laser light source;
   a line illuminator for converting laser light from the source to a line of radiation, the line illuminator including a collimator arranged to receive the laser light from the source and an aspherical lens for converting collimated light from the collimator to the line of radiation;

a second fiber optic cable coupled to the first single mode fiber optic cable at one end thereof and to the line illuminator at another end thereof, at least one of the fiber optic cables being a single mode fiber optic cable; and a focusing device for simultaneously directing the line of radiation onto sites of a microarray in one dimension of a two-dimensional plane at the surface of the microarray.

20. A system for imaging a microarray comprising:

first and second laser light sources, each source configured to output laser light in a different predetermined frequency band;

first and second single mode fiber optic cables coupled to the first and second laser light sources, respectively, for transmitting laser light in single mode transmission; and first and second line illuminators coupled to the first and second single mode fiber optic cables, respectively, for converting laser light from the respective source to a line of radiation, the line illuminators each including a collimator arranged to receive the laser light from the source and an aspherical lens for converting collimated light from the collimator to the line of radiation; and a focusing device for simultaneously directing the line of radiation onto sites of a microarray in one dimension of a two-dimensional plane at the surface of the microarray.

21. The system of claim 20, further comprising:

a combiner for combining the lines of radiation from the first and second illuminators;

means for confocally irradiating the microarray with the combined lines of radiation and for returning radiation from the microarray; and a detector for receiving the returned radiation and for generating signals for use in analysis of the microarray.

22. A method for making a system for imaging a microarray comprising:

placing a laser light source, a line illuminator, a focusing device and a stage in a configuration wherein:

the laser light source is coupled to the line illuminator via a single mode fiber optic cable, the fiber optic cable configured for transmitting laser light from the source in single mode transmission, and the line illuminator configured for converting laser light from the source to a line of radiation, the line illuminator includes a collimator arranged to receive the laser light from the source and an aspherical lens for converting collimated light from the collimator to the line of radiation;

the focusing device simultaneously directs the line of radiation onto sites of a microarray in one dimension of a two-dimensional plane; and the stage is configured to place the microarray surface at the plane.

23. A method for imaging a microarray comprising:

generating laser light;

transmitting the laser light to a line illuminator via a single mode fiber optic cable, the fiber optic cable configured for transmitting laser light from the source in single mode transmission, and the line illuminator configured for converting laser light from the source to a line of radiation, the line illuminator including a collimator arranged to receive the laser light from the source and an aspherical lens for converting collimated light from the collimator to the line of radiation; and directing the line of radiation with a focusing device, wherein the line of radiation is simultaneously directed onto sites of a microarray in one dimension of a two-dimensional plane at the surface of the microarray.

24. A method for imaging a microarray comprising:

generating laser light at first and second wavelengths;

transmitting the first and second wavelength laser light to respective line illuminators via respective first and second single mode fiber optic cables, each fiber optic cable configured for transmitting laser light from the respective source in single mode transmission, and each line illuminator configured for converting laser light from the respective source to a line of radiation, each line illuminator including a collimator arranged to receive the laser light from the source and an aspherical lens for converting collimated light from the collimator to the line of radiation;

combining the lines of radiation from the line illuminators;

directing the combined lines of radiation with a focusing device, wherein the line of radiation is simultaneously directed onto sites of a microarray in one dimension of a two-dimensional plane at the surface of the microarray, thereby confocally irradiating the microarray with the combined lines of radiation; and directing radiation returned from the microarray to a detector configured to generate signals for analysis of the microarray.

25. The system of claim 19, wherein the line illuminator is configured to convert laser light from the source to a line of radiation of substantially uniform intensity over a desired line length.

26. The system of claim 19, wherein the collimator and aspherical lens are prealigned within a module to permit installation of the module in the system without further alignment within the module during installation.

27. The system of claim 19, wherein the focusing device is configured to create a uniform line of radiation that is diffraction limited in the narrow dimension of the line.

28. The system of claim 26, further comprising a laser line filter disposed in the module intermediate the collimator and the aspherical lens.

29. The system of claim 19, wherein individual sites on the microarray are separated by a distance in the range of about 0.1 to 50 micrometers, and wherein the system is configured to distinguish the individual sites.

30. The system of claim 19, wherein the system is configured to obtain an image of the microarray at a Rayleigh resolution between about 0.2 and 10 micrometers.

31. The system of claim 20, wherein the line illuminators are configured to convert laser light from the source to lines of radiation of substantially uniform intensity over a desired line length.

32. The system of claim 20, wherein the collimator and aspherical lens are prealigned within a module to permit installation of the module in the system without further alignment within the module during installation.

33. The system of claim 20, wherein the focusing device is configured to create uniform lines of radiation that are diffraction limited in the narrow dimension of the line.

34. The system of claim 32, further comprising a laser line filter disposed in the module intermediate the collimator and the aspherical lens.

35. The system of claim 20, wherein individual sites on the microarray are separated by a distance in the range of about 0.1 to 50 micrometers, and wherein the system is configured to distinguish the individual sites.

36. The system of claim 20, wherein the system is configured to obtain an image of the microarray at a Rayleigh resolution between about 0.2 and 10 micrometers.

37. The method of claim 23, wherein the line illuminator converts laser light from the source to a line of radiation of substantially uniform intensity over a desired line length.

38. The method of claim 23, wherein the focusing device creates a uniform line of radiation that is diffraction limited in the narrow dimension of the line.

39. The method of claim 23, wherein individual sites on the microarray are separated by a distance in the range of about 0.1 to 50 micrometers, and wherein the individual sites are distinguished by the method.

40. The method of claim 23, wherein an image of the microarray is obtained at a Rayleigh resolution between about 0.2 and 10 micrometers.

41. The method of claim 24, wherein the line illuminators convert laser light from the source to lines of radiation of substantially uniform intensity over a desired line length.

42. The method of claim 24, wherein the focusing device creates uniform lines of radiation that is diffraction limited in the narrow dimension of the line.

43. The method of claim 24, wherein individual sites on the microarray are separated by a distance in the range of about 0.1 to 50 micrometers, and wherein the individual sites are distinguished by the method.

44. The method of claim 24, wherein an image of the microarray is obtained at a Rayleigh resolution between about 0.2 and 10 micrometers.

\* \* \* \* \*